United States Patent
Kluge et al.

(10) Patent No.: US 10,765,464 B2
(45) Date of Patent: Sep. 8, 2020

(54) BONE CEMENT MIXING DEVICE WITH SPACER IN AN AMPOULE RECEPTACLE

(71) Applicant: Heraeus Medical GmbH, Wehrheim (DE)

(72) Inventors: Thomas Kluge, Vallendar (DE); Rainer Strathausen, Friedrichsdorf (DE); Sebastian Vogt, Erfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 138 days.

(21) Appl. No.: 16/220,258

(22) Filed: Dec. 14, 2018

(65) Prior Publication Data
US 2019/0183552 A1 Jun. 20, 2019

(30) Foreign Application Priority Data
Dec. 15, 2017 (DE) .......................... 10 2017 130 084

(51) Int. Cl.
*A61B 17/88* (2006.01)
*B01F 15/02* (2006.01)

(52) U.S. Cl.
CPC ...... *A61B 17/8833* (2013.01); *A61B 17/8822* (2013.01); *B01F 15/0206* (2013.01);
(Continued)

(58) Field of Classification Search
CPC . A61B 17/88; A61B 17/8802; A61B 17/8805; A61B 17/8822; A61B 17/8827;
(Continued)

(56) References Cited

U.S. PATENT DOCUMENTS 4,613,326 A * 9/1986 Szwarc ................ A61M 5/284
604/218
4,671,263 A 6/1987 Draenert
(Continued)

FOREIGN PATENT DOCUMENTS

DE 3640279 6/1987
DE 4030832 7/1991
(Continued)

OTHER PUBLICATIONS

Charnley, J., "Anchorage of the Femoral Head Prosthesis of the Shaft of the Femur," The Journal of Bone and Joint Surgery, 42 B, No. 1, pp. 28-30 (Feb. 1960).
(Continued)

*Primary Examiner* — Eric S Gibson
(74) *Attorney, Agent, or Firm* — Dicke, Billig & Czaja, PLLC

(57) ABSTRACT

One aspect relates to a device to produce a bone cement paste from a monomer liquid and a cement powder as starting components of the bone cement paste, and to dispense the mixed bone cement paste. The device includes a cartridge with a cylindrical interior, a dispensing plunger movable towards the front of the cartridge; a receptacle extending along a longitudinal direction, a front of the receptacle connected with the rear of the cartridge; a pumping plunger arranged and in the receptacle movable towards the front of the receptacle; a breakable ampoule containing the monomer liquid, the ampoule with ampoule body arranged in the receptacle between the pumping plunger and the dispensing plunger with at least some sections of the ampoule body in contact with the receptacle; and a spacer arranged in the receptacle between the dispensing plunger and the ampoule body, the spacer extending in the longitudinal direction of the receptacle and the spacer being sepa-
(Continued)

rated from the inner wall of the receptacle by a distance at least as large as the wall thickness of the ampoule body.

21 Claims, 16 Drawing Sheets

(52) U.S. Cl.
CPC ...... *B01F 15/0237* (2013.01); *B01F 15/0279* (2013.01); *A61B 17/8827* (2013.01); *B01F 2215/0029* (2013.01)

(58) Field of Classification Search
CPC ......... A61B 17/8833; A61B 2017/8838; B01F 15/0206; B01F 15/0237; B01F 15/0278; B01F 15/0279; B01F 2215/0029
See application file for complete search history.

(56) References Cited

U.S. PATENT DOCUMENTS

| | | | |
|---|---|---|---|
| 4,758,096 A | 7/1988 | Gunnarsson | |
| 4,973,168 A * | 11/1990 | Chan | A61B 17/8805 |
| | | | 206/219 |
| 5,100,241 A | 3/1992 | Chan | |
| 5,193,907 A | 3/1993 | Faccioli et al. | |
| 5,344,232 A | 9/1994 | Nelson et al. | |
| 5,586,821 A | 12/1996 | Bonitati et al. | |
| 5,588,745 A | 12/1996 | Tanaka et al. | |
| 5,624,184 A | 4/1997 | Chan | |
| 5,997,544 A * | 12/1999 | Nies | A61B 17/8802 |
| | | | 606/92 |
| 6,033,105 A | 3/2000 | Barker et al. | |
| 6,709,149 B1 | 3/2004 | Tepic | |
| 8,132,959 B2 * | 3/2012 | Smit | A61B 17/8833 |
| | | | 206/222 |
| 8,690,419 B2 * | 4/2014 | Faccioli | A61B 17/8833 |
| | | | 366/139 |
| 10,639,088 B2 * | 5/2020 | Vogt | A61B 17/8816 |
| 2006/0164913 A1 * | 7/2006 | Arramon | B01F 15/0215 |
| | | | 366/139 |
| 2016/0100875 A1 * | 4/2016 | Faccioli | B01F 13/0023 |
| | | | 606/94 |
| 2018/0132917 A1 * | 5/2018 | Vogt | A61B 17/8833 |
| 2018/0132919 A1 * | 5/2018 | Vogt | B01F 15/0206 |
| 2018/0256233 A1 * | 9/2018 | Vogt | B01F 15/0237 |
| 2018/0289406 A1 * | 10/2018 | Vogt | C04B 26/06 |
| 2018/0360515 A1 * | 12/2018 | Vogt | B01F 13/0023 |
| 2019/0183552 A1 * | 6/2019 | Kluge | A61B 17/8822 |
| 2019/0216516 A1 * | 7/2019 | Vogt | A61B 17/8822 |
| 2020/0179023 A1 * | 6/2020 | Vogt | A61B 17/8833 |
| 2020/0179024 A1 * | 6/2020 | Vogt | B01F 3/1221 |

FOREIGN PATENT DOCUMENTS

| | | | |
|---|---|---|---|
| DE | 102009031178 | 9/2010 | |
| DE | 102016121607 | 5/2017 | |
| EP | 0692229 | 1/1996 | |
| EP | 0796653 | 9/1997 | |
| EP | 1005901 | 6/2000 | |
| EP | 1016452 | 7/2000 | |
| EP | 1020167 | 7/2000 | |
| EP | 1886647 | 2/2008 | |
| JP | 2019107449 A * | 7/2019 | .......... B01F 15/0223 |
| WO | 9426403 | 11/1994 | |
| WO | 9967015 | 12/1999 | |
| WO | 0035506 | 6/2000 | |

OTHER PUBLICATIONS

Kühn, Klaus-Dieter, "Bone Cements," Springer-Verlag, pp. 9 (2000).

* cited by examiner

US 10,765,464 B2

BONE CEMENT MIXING DEVICE WITH SPACER IN AN AMPOULE RECEPTACLE

CROSS-REFERENCE TO RELATED APPLICATION

This Utility Patent Application claims priority to Application No. DE 102017130084.8, filed on Dec. 15, 2017, which is incorporated herein by reference.

TECHNICAL FIELD

One aspect relates to a device to produce a bone cement paste from a monomer liquid and a cement powder as the starting components of the bone cement paste, and to dispense the mixed bone cement paste.

One aspect also relates to a method to produce a bone cement paste, for example, a pasty polymethyl methacrylate bone cement paste.

One aspect relates to a device to store, mix and apply polymethyl methacrylate bone cement. The device is intended in one embodiment for cementing total joint endoprostheses. The device according to one embodiment is a full pre-packed cementing system.

BACKGROUND

Polymethyl methacrylate (PMMA) bone cements are based on the fundamental work done by Sir Charnley (Charnley, J.: Anchorage of the femoral head prosthesis of the shaft of the femur. J. Bone Joint Surg. 42 (1960) 28-30). Conventional polymethyl methacrylate bone cements (PMMA bone cements) are composed of a powdery component and a liquid monomer component (K.-D. Kuhn: Knochenzemente für die Endoprothetik: Ein aktueller Vergleich der physikalischen und chemischen Eigenschaften handelsüblicher PMMA-Zemente. Springer-Verlag Berlin Heidelberg New York, 2001). The monomer component generally contains the monomer methyl methacrylate and an activator dissolved therein (N,N-dimethyl-p-toluidine). The powder component, also called cement powder or bone cement powder, contains one or more polymers which are manufactured by polymerisation, for example suspension polymerisation, on the basis of methyl methacrylate and co-monomers such as styrene, methyl acrylate or similar monomers, an X-ray opaque component and the initiator dibenzoyl peroxide. When the powder component is mixed with the monomer component, the swelling of the polymers of the powder components in the methyl methacrylate creates a plastically workable paste; this paste is the actual bone cement or bone cement paste. When the powder component is mixed with the monomer component, the N,N-dimethyl-p-toluidine activator reacts with dibenzoyl peroxide forming radicals in the process.

The radicals formed initiate the radical polymerisation of the methyl methacrylate. As the polymerisation of the methyl methacrylate progresses, the viscosity of the bone cement paste increases until it sets.

PMMA bone cements can be mixed in suitable mixing vessels with the aid of spatulas by mixing the cement powder with the monomer liquid. This may result in the inclusion of air bubbles in the bone cement paste, which can have a negative impact on the mechanical properties of the bone cement when it has set.

A large number of vacuum cementing systems have been disclosed whose aim was to prevent air inclusions in the bone cement paste; the following systems are stated by way of example: U.S. Pat. Nos. 6,033,105A, 5,624,184A, 4,671,263A, 4,973,168A, 5,100,241A, WO 99/67015 A1, EP 1 020 167 A2, U.S. Pat. No. 5,586,821A, EP 1 016 452 A2, DE 36 40 279 A1, WO 94/26403 A1, EP 1 005 901 A2, EP 1 886 647 A1, U.S. Pat. No. 5,344,232 A.

A further development in the cementing technique are cementing systems where the cement powder as well as the monomer liquid are already packed in separate compartments of the mixing devices and mixed with each other in the cementing system only when the cement is to be applied immediately. Such closed full pre-packed mixing devices were proposed with EP 0 692 229 A1, DE 10 2009 031 178 B3, U.S. Pat. Nos. 5,997,544 A, 6,709,149 B1, WO 00/35506 A1, EP 0 796 653 A2 and U.S. Pat. No. 5,588,745 A.

The patent DE 10 2009 031 178 B3 discloses a storage and mixing device as a full pre-packed mixing device, in which the starting components necessary to produce the bone cement paste are already stored in the storage and mixing device and can be brought together and mixed in the storage and mixing device. The storage and mixing device has a two-part dispensing plunger to close a cement cartridge. A combination of a gas-permeable sterilisation plunger and a gas-impermeable sealing plunger is used here.

Polymethyl methacrylate bone cements are applied in the not yet fully set, pasty state as bone cement paste after the cement powder has been mixed with the liquid monomer components. When mixing devices are used, the bone cement paste is located in a cartridge when the cement used is a powder-liquid cement. When these conventional PMMA bone cements are applied, the bone cement paste formed after the two starting components have been mixed is extruded with the aid of manually operated extrusion devices. The bone cement paste is extruded from the cartridge by moving a dispensing plunger. The dispensing plungers usually have a diameter of 30 mm to 40 mm and therefore an area of 7.0 cm$^2$ to 12.5 cm$^2$ on the outside, where a pushrod or a rod of the extrusion device acts during the extrusion process. The movement of the dispensing plunger is, for example, brought about by manually operated, mechanical extrusion devices. These manual extrusion devices normally achieve an extrusion force in the range of approx. 1.5 kN to 3.5 N.

These simple mechanical extrusion devices use clamping rods for the extrusion, which are driven by a manually operated toggle lever. The manually driven extrusion devices have been tried-and-tested around the globe for many decades and currently represent the Prior Art. The advantage of these extrusion devices is that the medical user has a feeling for the penetration resistance of the bone cement paste into the bone structures (cancellous bone) via the manual force they need to apply.

When using all the full pre-packed mixing devices known to date, the medical user has to carry out several operating steps on the devices in a predetermined order one after the other, until the mixed bone cement paste is available and can be applied. Executing the operating steps in the incorrect order can cause the mixing device to fail and thus cause disruptions to the surgical operating procedure. Expensive training courses for the medical users are therefore required to prevent user errors.

WO 00/35506 A1 proposes a device where the polymethyl methacrylate cement powder is stored in a cartridge, the cement powder filling the whole volume of the cartridge and the spaces between the particles of the cement powder having a volume which corresponds to the volume of the monomer liquid which is necessary to produce bone cement paste with the cement powder stored in the cartridge. This device is designed such that the monomer liquid is introduced into the cartridge from the top through the action of a vacuum, a vacuum being applied for this purpose at a vacuum connector on the underside of the cartridge. The monomer liquid is thereby pulled through the cement powder, whereby the air in the spaces between the cement powder particles is displaced by the monomer liquid. This obviates the need for the cement paste formed to be subjected to a thorough mechanical mixing with a mixer.

The disadvantage of this system is that cement powders which swell quickly with the monomer liquid cannot be mixed with this device, because the fast swelling particles of cement powder form a gelatinous barrier after the monomer liquid has penetrated around 1 to 2 cm into the cement powder and hinder the migration of the monomer liquid through all of the cement powder. Conventional cement powders additionally exhibit the phenomenon that the particles of cement powder are wetted only badly by methyl methacrylate because they have different surface energies. This means the methyl methacrylate only penetrates relatively slowly into the cement powder. When a vacuum is used, it is furthermore not possible to exclude the fact that after the monomer liquid has completely penetrated through the cement powder, the monomer liquid is removed by suction via the vacuum connection. Insufficient monomer liquid is then available for the paste to set by radical polymerisation, or the ratio of the mixture is changed unintentionally and hence the consistency of the bone cement paste, too. A further problem is that the air trapped between the cement powder particles by the monomer liquid should be displaced from the top to the bottom, because the air, which has a lower specific weight than the monomer liquid, has the tendency because of gravity to migrate to the top in the cement powder and not to the bottom towards the vacuum connection.

DE 10 2016 121 607, which was not published in advance, proposes a full pre-packed mixing system with a cartridge containing a cement powder to produce a bone cement paste. A dispensing plunger is provided in the cartridge, and a receptacle with a monomer liquid container is arranged behind the cartridge. On the rear of the receptacle is a pumping plunger which can be used to squash the monomer liquid container and to press the monomer liquid out of the receptacle and into the cartridge.

Practical tests have illustrated that the bone cement paste produced with this device always has a good consistency when a suitable cement powder is used. If the squashed monomer liquid container is compressed to the maximum extent as the monomer is being transferred, then a good cement paste is reproducibly obtained. If the burst monomer liquid container is not fully compressed, residue of monomer liquid can remain between the dispensing plunger and the pumping plunger within the fragments of the burst monomer liquid container, which can escape at the end of the extrusion of the cement paste by a subsequent post-compression of the burst monomer liquid container as a consequence of an axial movement of the pumping plunger towards the dispensing plunger. This monomer liquid residue can change the consistency of the bone cement paste as it is being dispensed. Undesired monomer bubbles can form in the bone cement paste as well.

For these and other reasons, a need exists for the present embodiments.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
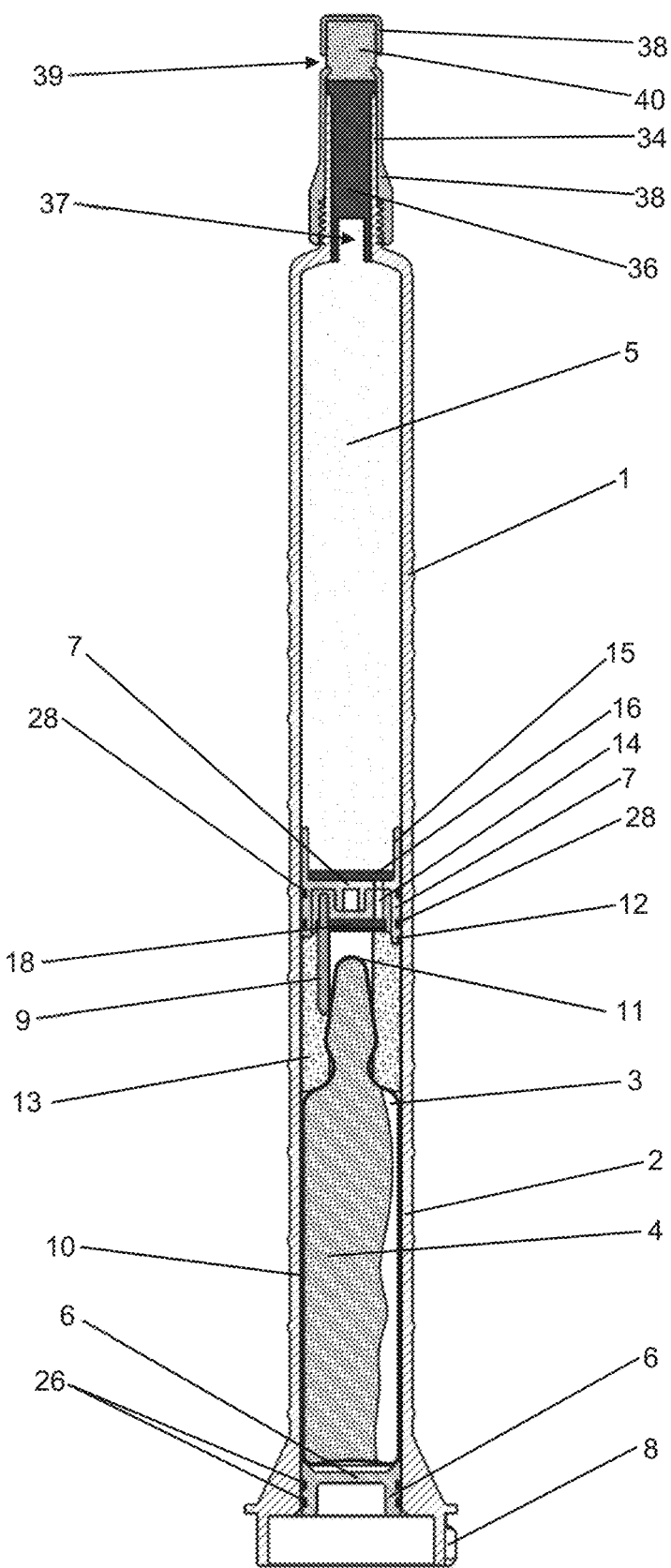
FIG. 1: illustrates a schematic cross-sectional view of an exemplary first device according to one embodiment to produce a bone cement paste.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

One embodiment consists in overcoming the disadvantages of the Prior Art. One embodiment consists in developing a device which is intended and suitable for mixing the bone cement paste from the starting components, and a method to produce a bone cement paste, in one embodiment, a pasty polymethyl methacrylate bone cement paste, whereby the bone cement paste is produced from a cement powder and a monomer liquid, with which the disadvantages of the previous devices and methods are overcome. One embodiment improves such a device such that the finished bone cement paste remains homogeneous while it is being dispensed as well. In addition, no monomer bubbles should be created in the bone cement paste thus produced, if possible. After the monomer has been transferred, the device and the method effectively prevent a post-densification of the glass shards from the burst glass ampoule at the start of and during the dispensing of the bone cement paste formed, to prevent monomer liquid subsequently being injected into the bone cement paste. A subsequent compression of the glass shards must be reproducibly excluded. Furthermore, the bone cement paste is to be provided in a consistency and quality which can be reproduced as accurately as possible.

One embodiment of the method is therefore to facilitate a situation where a homogeneous bone cement paste can be produced and applied even when the device has a very simple and low-cost design and at the same time the device is very easy and uncomplicated to use from the start to the end of the extrusion procedure.

In one embodiment, the device is driven by a simple, conventional extrusion device and is as simple as possible to operate. The design in one embodiment is low cost so that the device can be used only once for reasons of hygiene. Many or all of the processes taking place in the device, such as the mixing of the starting components, the opening of the monomer liquid container and, where possible, also the dispensing of the bone cement paste and, where possible, the opening of the cartridge as well, shall in one embodiment be undertaken with as few operating steps as possible and be automated as far as possible and in one embodiment such that it can be driven with only one linear drive.

The operation of the device in one embodiment is simplified as much as possible to fundamentally prevent application errors which arise from incorrectly carried out assembly steps. After removing the device from its packaging, the medical user is be able to connect it to an extrusion device and then operate it. The design of the device in one embodiment obviates the need for any further assembly and operating steps. The device in one embodiment also allows the safe storage of cement powder and monomer liquid in compartments separated from each other so that an unintentional mixing of the cement components while the device is being stored is excluded. The device in one embodiment is sterilised with the gas ethylene oxide. The cement powder stored in the device is accessible to ethylene oxide for this purpose, if applicable. It shall be possible in one embodiment to activate the device in the operating theatre with the aid of a manually driven extrusion device so that, after the device has been connected with the extrusion device via a form-fit or force-fit connection, operating the extrusion device causes the axially advancing rod of the extrusion device to act on the device, opens the monomer liquid container and subsequently transfers the monomer liquid into the cement powder as the rod continues to move. In one embodiment, the mixing of the monomer liquid with the cement powder shall take place without a mixer which has to be moved manually from the outside. If possible, the mixing of the cement components to form the bone cement paste and in one embodiment the extrusion of the mixed bone cement paste as well shall be performed only by virtue of the forward movement of the rod of the extrusion device.

The objectives of the embodiments are achieved by a device to produce a bone cement paste from a monomer liquid and a cement powder as the starting components of the bone cement paste, and to dispense the mixed bone cement paste, the device in one embodiment including:

1) a cartridge with a cylindrical interior, a dispensing plunger which can move towards a front of the cartridge, being arranged in the rear of the cartridge inside the cartridge, a receptacle which extends along a longitudinal direction, a front side of the receptacle being connected to the rear of the cartridge, 2) a pumping plunger arranged in the receptacle, the pumping plunger being supported in the receptacle so as to be movable in the longitudinal direction of the receptacle towards the front of the receptacle, 3) a crushable ampoule containing the monomer liquid, the ampoule being arranged in the receptacle between the pumping plunger and the dispensing plunger and the ampoule having an ampoule body, the ampoule body being in contact with the inner wall of the receptacle at least in parts, and 4) a spacer arranged in the receptacle between the dispensing plunger and the ampoule body or between the pumping plunger and the ampoule body, the spacer extending in the longitudinal direction of the receptacle and the separation of the spacer from the inner wall of the receptacle being at least as large as the wall thickness of the ampoule body.

According to one embodiment, a spacer can theoretically also be arranged between the dispensing plunger and the ampoule body, and a second spacer between the pumping plunger and the ampoule body. The ampoule is then crushed between the two spacers. One embodiment thus does not provide for precisely one spacer, since a further (second) spacer can also be provided. The spacer or spacers here can also consist of several parts. According to one embodiment, however, it is provided for the spacer to consist of one part or for the spacers to consist of one part. Likewise, according to one embodiment, the monomer liquid can be arranged between the pumping plunger and the dispensing plunger in the receptacle, the liquid being contained in more than one ampoule. The ampoules are then broken open sequentially or in parallel.

The device according to one embodiment is suitable for and provided for storing the monomer liquid. In one embodiment device also provides for the storage of the cement powder.

The receptacle, the cartridge, the pumping plunger, the dispensing plunger and the spacer are in one embodiment made from a thermoplastic material, for example, by means of an injection moulding method. This means that the device can be manufactured at low cost as a hygienic, disposable product.

The interior of the cartridge has a cylindrical geometry. The cylindrical form is the simplest form whereby the interior of the cartridge can be realized. Geometrically, a cylindrical form is understood to be the form of a general cylinder with an arbitrary base area, that is, not only a cylinder with a circular base. The inner wall of the interior of the cartridge can therefore be realized by the cylindrical surface of a cylinder with an arbitrary base, particularly with a different base, that is, with bases which are not circular or not round. According to one embodiment, a cylindrical geometry with rotational symmetric and for example, circular base is preferred in one embodiment for the interior, however, because this is the simplest to manufacture. The same applies to the cylindrical interior of the receptacle.

Devices according to embodiments can provide for the spacer to be fastened to the rear of the dispensing plunger or the front of the pumping plunger or for the spacer to be arranged around an ampoule head of the ampoule, the ampoule head having a smaller outer diameter than the ampoule body.

When the spacer is fastened to the rear of the dispensing plunger or the front of the pumping plunger, the device is particularly easy to set up. The position of the spacer is thus fixed and it cannot tilt, thus ensuring the spacer moves stably and reliably against the ampoule. Theoretically, a spacer can also be fastened to the rear of the dispensing plunger and a second spacer to the front of the pumping plunger as well. Depending on which plunger (pumping plunger or dispensing plunger) the spacer is fastened to (or when the spacer is fastened to both plungers), no shards of the ampoule can find their way between the plunger in question and the spacer and thus tilt the spacer and/or change the separation between the two plungers which is to be restricted by the spacer.

There can further be provision for at least one cutting element with a cutting edge to be arranged on the front of the pumping plunger facing the ampoule and/or the rear of the dispensing plunger facing the ampoule, in one embodiment at least three or at least four cutting elements each with at least one cutting edge, where the at least one cutting element is arranged on a part of the front of the pumping plunger and/or the rear of the dispensing plunger which is located towards the inner wall of the receptacle so that the at least one cutting element cuts through the wall of the ampoule body when the pumping plunger is driven forwards, the cutting edge in one embodiment extending radially away from a central longitudinal axis of the pumping plunger and/or the dispensing plunger.

This causes the ampoule or the ampoule body to break or be cut at defined places. The breaking open process can thus be better controlled and the procedure can be standardised. Shards of the ampoule can thus be produced in a predictable size which fit well into the space generated by the spacer. The fact that the at least one cutting element is arranged on a part of the front of the pumping plunger and/or the rear of the dispensing plunger positioned towards the inner wall of the receptacle does not mean that the at least one cutting element cannot also extend to the middle of the front of the pumping plunger and/or the rear of the dispensing plunger. It must then be arranged at least in an outer part which is arranged towards the inner wall of the receptacle as well so that it is flush with the wall of the ampoule body in the longitudinal direction. By applying a defined force at a predefined and localised point, the pressure at this point can be increased for the same force and a defined breakage of the ampoule can thus be achieved. The process of breaking open the ampoule thus becomes more reproducible.

The outside of at least one cutting element is in one embodiment in contact with the inner wall of the receptacle.

Provision can be made for a free end of the spacer to have a separation to the at least one cutting element, in one embodiment a separation in the longitudinal direction of at least 10 mm.

Devices with cutting elements according to one embodiment can provide for the ampoule to have an ampoule head with a smaller diameter than the ampoule body and for the at least one cutting element and the spacer to be arranged on the rear of the dispensing plunger, with the ampoule head pointing towards the dispensing plunger, or for the at least one cutting element and the spacer to be arranged on the front of the pumping plunger with the ampoule head pointing towards the pumping plunger.

This means that the ampoule can be opened with certainty. In addition, the breaking front which is generated by the at least one cutting element when the ampoule is opened runs behind the free end of the spacer so that the shards of the ampoule do not find their way between the free ends of the spacer and the pumping plunger or the dispensing plunger which is to be moved towards it and thus unintentionally increase the distance created by the spacer between the dispensing plunger and pumping plunger which are pushed together.

According to one embodiment, provision can be made for the ampoule body to be the part of the ampoule with the largest cross-section perpendicular to the longitudinal direction of the receptacle. This ensures that the ampoule has a large capacity and the device can have a relatively compact design, that is, is not too long in the longitudinal direction.

Furthermore, provision can be made for the spacer in the longitudinal direction to be at least three times as long as the at least one cutting element is separated in the longitudinal direction from the front of the pumping plunger or the rear of the dispensing plunger, the spacer in one embodiment being at least five times as long in the longitudinal direction as the at least one cutting element is separated in the longitudinal direction from the front of the pumping plunger or the rear of the dispensing plunger.

This creates a situation where the breaking front which is generated by the at least one cutting element when the ampoule is opened runs sufficiently far behind the free ends of the spacer that the shards of the ampoule do not or do not so easily find their way between the free ends of the spacer and the pumping plunger or the dispensing plunger which is to be moved towards it, and thus unintentionally increase the distance created by the spacer between the dispensing plunger and pumping plunger which are pushed together.

In accordance with one embodiment, provision can be made for the spacer to block a further reduction of the separation between the pumping plunger and the dispensing plunger after the ampoule is opened and after the ampoule is compressed when the pumping plunger is driven forwards so that shards of the ampoule find room between the dispensing plunger and the pumping plunger without being broken into smaller shards when the pumping plunger and the dispensing plunger with the spacer in between are moved towards the front of the cartridge.

The shards of the ampoule can already have been broken several times when the ampoule is compressed (in temporal sequence as well), before they are no longer broken into (even) smaller shards.

This brings about a situation where, after the spacer has fixed the distance between the pumping plunger and the dispensing plunger, no further compressions can take place as the pumping plunger and the dispensing plunger are driven forwards together by shards breaking later, which further reduce the space between the pumping plunger and the dispensing plunger and thus push more monomer liquid into the interior of the cartridge, which then finds its way into the bone cement paste as monomer bubbles or changes the consistency of the bone cement paste during the dispensing process.

Provision can in one embodiment also be made for the spacer to have a length in the longitudinal direction so that the volume between the pumping plunger and the dispensing plunger at a distance corresponding to the length of the spacer is larger than the volume of the material of the ampoule, in one embodiment at least twice as large as the volume of the ampoule material or at least as large as the volume of the shards of the broken ampoule including all intermediate spaces.

This can ensure that the glass shards do not have to be compressed with a very large force, or that the force which arises as the bone cement paste is being extruded during the joint movement of the pumping plunger and the dispensing plunger does not cause any further splintering of the ampoule shards which further reduce the volume between the pumping plunger and the dispensing plunger and thus unintentionally press additional monomer liquid into the bone cement paste in the interior of the cartridge. This can ensure that the bone cement paste is homogeneous.

One embodiment proposes that the spacer is realized by a plurality of rods which extend in the longitudinal direction, the rods being connected to each other or fastened to the front of the pumping plunger or fastened to the rear of the dispensing plunger, whereby the rods in one embodiment have a round, triangular or angular cross-section, for example, rectangular, and/or have a T-shaped longitudinal section.

The rods themselves do not take up much space, and can stabilise the separation between the pumping plunger and dispensing plunger at two points at least. The rods can in one embodiment taper to a point at their free ends so that these can drill well through the wall of the ampoule in front of the ampoule body. In addition, the rods can easily push aside shards of the ampoule. The spacer is in one embodiment realized by at least three rods, in one embodiment by three, four, five or six rods.

According to one embodiment, provision can be made for the spacer to be realized by a hollow cylinder, for example, by a hollow cylinder with several slits in the longitudinal direction.

Furthermore, provision can be made for the ampoule to have an ampoule head which is connected to the ampoule body, the ampoule head having a smaller outer diameter than the ampoule body and the spacer being arranged next to the ampoule head or the spacer surrounding the ampoule head.

The motion of the spacer can thus be defined in a simple way and the breaking open process can be standardised. In addition, the ampoule is thus firmly held and stored in the device.

Furthermore, provision can be made for the ampoule to be made of glass or a synthetic material which is chemically stable against the monomer liquid, glass being preferred in one embodiment as the material for the ampoule.

These materials are well suited for the storage of the monomer liquid.

Provision can also be made for the ampoule body to be cylindrical and for the receptacle to have a cylindrical interior, where in one embodiment the outer diameter of the ampoule body matches the inner diameter of the receptacle which is cylindrical inside so that the ampoule body is held in the receptacle, for example, held flush with the surface.

The ampoule is thus firmly held in the device so that it cannot accidentally break open prematurely in the device by being knocked.

The provision can in one embodiment be that the pumping plunger is held so that it can be driven forwards from the rear of the receptacle to the front in the longitudinal direction.

This means that the device can be clamped into an extrusion device such as a cartridge gun, and operated with it.

Provision can be made for the interior of the cartridge on the front to be sealed apart from one dispensing aperture to expel the bone cement paste, whereby the dispensing plunger in the interior of the cartridge can be pressed towards the dispensing aperture.

The bone cement paste can thus be extruded through this dispensing aperture.

Provision can thus be made for a dispensing aperture of the cartridge on whose front it is to be sealed on its front with a seal, for example, with a plug, whereby the bone cement paste can be extruded from the cartridge through the dispensing aperture when the dispensing aperture is open, and whereby the seal is in one embodiment permeable to gases and impermeable to the cement powder. The seal is in one embodiment a filter, for example, a pore filter, which is permeable to gases and impermeable to the cement powder.

The cement powder can thus be stored well in the interior of the cartridge. The seal can be opened. The interior of the cartridge and the cement powder can be sterilised by evacuating and rinsing the interior of the cartridge with a sterilizing gas, such as ethylene oxide, through the seal, when it is permeable to gases and impermeable to the cement powder.

Provision can be made here for the seal to have a recess at the rear which points towards the interior of the cartridge, in which the front part of the cement powder is contained. This part can then be removed later with the seal so that part of the bone cement paste which is less well mixed is removed with the stopper.

The seal in one embodiment together with the dispensing plunger forms a sealing system of the cartridge which can be opened by pressure acting as axial pressure on the dispensing plunger in the direction of the dispensing aperture.

A development of one embodiment can provide for the rear of the cartridge to be connected to the front of the receptacle in such a way that the interior of the cartridge is flush with the interior of the receptacle.

This ensures that the pumping plunger can be driven forwards together with the dispensing plunger into the interior of the cartridge to extrude the bone cement paste out of the interior of the cartridge.

It is preferable in one embodiment that provision can also be made for the cement powder in the interior of the cartridge to be arranged between the front of the cartridge and the dispensing plunger, an additive which conducts the monomer liquid preferably in one embodiment being distributed in the cement powder.

The device can thus be used immediately and does not have to be filled with cement powder in advance.

There can also be a provision for the cement power to be in contact with the front of the dispensing plunger, to make contact across the whole area, the cement powder preferably in one embodiment being pressed into the interior of the cartridge.

This prevents larger gas inclusions remaining in the cartridge, which could lead to gas inclusions in the bone cement paste when the monomer liquid is mixed with the cement powder. This cannot happen with a densely packed cement powder, since the monomer liquid wets the particles of the cement powder well, and the surface tension of the monomer liquid then does not allow any gas inclusions between the particles of the cement powder, or at least no inclusions of relevance.

There can also be a provision that the volume of the spaces between the cement particles of the cement powder in the interior of the cartridge ranges from 22 percent volume to 40 percent volume relative to the total volume of the cement powder. The total volume of the cement powder preferably in one embodiment corresponds to the volume of the interior of the cartridge, which is bounded by the dispensing plunger and by a seal in a dispensing aperture at the front of the cartridge.

It can furthermore be provided that an additive which conducts the monomer liquid is distributed in the cement powder, the cement powder in one embodiment being coated with the additive or mixed with the additive.

A biocompatible cellulose can be used as the additive, for example, which exhibits sufficient absorbency for the monomer liquid. The additive can be distributed in the cement powder in the form of particles.

This allows the monomer liquid to quickly distribute itself in the cement powder and thus results in a complete mixing before the swelling cement powder would prevent a further spreading of the monomer liquid. This makes it possible for the monomer liquid to be conducted over longer distances through the cement powder as well and thus also allows a homogeneous bone cement paste to be produced.

There can furthermore be a provision for a hydrophilic additive to be distributed in the cement powder, with which the monomer liquid can be distributed in all of the cement powder, in one embodiment without a prior polymerisation of the bone cement preventing the further distribution of the monomer liquid in the cement powder.

This allows the monomer liquid to be distributed rapidly in the cement powder before a polymerisation of the cement powder contained in the bone cement with the monomer liquid takes place and thus prevents a further distribution of the monomer liquid. This is the only way the design according to one embodiment in a cartridge which is moulded together with the receptacle is possible, namely that the monomer liquid is pressed from one side into the cement powder and can nevertheless distribute itself through all the cement powder before the polymerisation prevents a further distribution of the monomer liquid in the cement powder.

The additive is in one embodiment particulate or fibrous. The additive in one embodiment contains a chemical substance with at least one OH group. The additive in one embodiment has an absorbency of at least 0.6 g methyl methacrylate per gram of additive.

One embodiment provides for the cement powder to contain at least a particulate polymethyl methacrylate or polymethyl methacrylate copolymer of the sieve fraction less than 100 µm, an initiator, and at least one particulate or fibrous additive which is insoluble in methyl methacrylate, the additive having an absorbency greater than or equal to 0.6 g methyl methacrylate per gram of additive at room temperature.

Such a cement powder is particularly well suited for distributing the monomer liquid in the cement powder so that the device can be designed such that a one-sided pressing in of the monomer liquid is possible on a narrow side of the interior of the cartridge as well. Surprisingly, it was found here that it is possible to produce a non-sticking, plastically deformable bone cement paste which hardens by itself through radical polymerisation by simply bringing such a cement powder into contact with a monomer liquid, without it being necessary to mix the cement paste manually or with the aid of technical devices. It was observed that by adding a particulate or fibrous additive which is insoluble in methyl methacrylate and has an absorbency greater than 0.6 g methyl methacrylate per gram of additive at room temperature to a cement powder of a low-viscosity bone cement produces a modified cement powder as the cement powder into which the monomer liquid can be pressed over a distance of at least 5 cm. Surprisingly, the additive also improves the wetting of the cement powder with monomer liquid. The additive here has a "wick effect" and conducts the monomer liquid into the interior of the cement powder even in very low quantities from 0.1% by weight. Furthermore, the additive slows down the sticking together of the polymer particles in the cement powder, which slows down the formation of a blocking gel layer and promotes the penetration of the monomer liquid into the cement powder. The monomer liquid here can be pressed into the cement powder or drawn in, too.

There can in one embodiment be a provision that the additive has covalently bonded hydroxyl groups on its surface. According to one embodiment, the additive can be selected from the group including microcrystalline cellulose, oxycellulose, starch, titanium dioxide and silicon dioxide, pyrotogenic silicon dioxide being preferred in one embodiment. The additive can have a particle size of the sieve fraction less than 100 µm, in one embodiment of the sieve fraction less than 50 µm, and in one embodiment of the sieve fraction less than 10 µm. Furthermore, there can be in one embodiment provision for the additive in the cement powder to be contained in the amount of 0.1 to 2.5% by weight relative to the total weight of the cement powder. Furthermore, there can be a provision that the polymer powder contains dibenzoyl peroxide as the initiator.

It is possible to provide for the monomer liquid to at least contain a methyl methacrylate and an activator. There can furthermore be a provision for the monomer liquid to contain at least one activator from the group of aromatic amines. There can furthermore be provision for the monomer liquid to contain at least one radical stabiliser from the group of the quinones or the sterically hindered phenols.

It is advantageous in one embodiment if the additive has covalently bonded hydroxyl groups on its surface. Advantageous in one embodiment are Si-OH groups and OH groups of alcohols. The additive has a high surface energy thanks to the OH groups arranged on its surface, which means the additive can be wetted well with methyl methacrylate. The pyrogenic silicic acids Aerosil® 380 and Aerosil® 300 are suitable. In addition, it is also possible to use silicon dioxide produced by sol/gel processes as the additive.

One embodiment also proposes that a hollow cylinder is arranged on the front of the dispensing plunger which blocks a further movement of the dispensing plunger towards the front of the cartridge so that sections of the dispensing plunger are a distance away from the front of the interior of the cartridge, and a dead volume remains in the interior of the cartridge when the dispensing plunger is pushed against the front of the interior of the cartridge.

This can prevent a part of the bone cement paste which is less well mixed and which is located in the vicinity of the dispensing plunger from being extruded at the end of the extrusion process. In addition, along the hollow cylinder the monomer liquid can be conducted deeper into a cement powder in the interior of the cartridge.

Provision can be made here for the dead volume to have a volume of at least 1 cm$^3$, in one embodiment at least 3 cm$^3$.

A development of one embodiment can provide for at least one connection which is permeable to the monomer liquid and gases, but impermeable to the cement power, to be provided in the dispensing plunger, the connection connecting the front of the dispensing plunger with the rear of the dispensing plunger or for an inner chamber of the receptacle and the interior of the cartridge to be connected to each other via a connection which is permeable to the monomer liquid and gases, but impermeable to the cement powder. The interior of the cartridge and the interior of the receptacle can thus be sterilised with a sterilising gas such as ethylene oxide. Additionally, the cement powder can be prevented from penetrating into the connection, reacting there prematurely with the monomer liquid after the ampoule is opened and thus sealing the connection with swelling bone cement paste, thereby hindering or preventing a further passage of the monomer liquid into the cement powder.

According to one embodiment, there can also be provision for at least one ventilation aperture to be arranged in the wall of the receptacle, the aperture connecting the interior of the receptacle with the outside. This allows even the interior of the device to be rinsed or even flushed with a sterilising gas such as ethylene oxide.

There can in one embodiment be provision for the at least one ventilation aperture to be arranged so close to the pumping plunger that it is sealed by a movement of the pumping plunger towards the front of the receptacle before the ampoule arranged in the receptacle is opened by the movement of the pumping plunger. The monomer liquid can thus be prevented from flowing out of the receptacle to the outside through the at least one ventilation aperture.

To facilitate the use of an extrusion device such as a cartridge gun, provision can also be made for a means of fastening an extrusion device to be arranged on the rear of the device, where the extrusion device can be used to press the pumping plunger and the dispensing plunger towards the front of the cartridge.

There can also be provision for a dispensing tube to be arranged on the front of the cartridge, whereby the bone cement paste can be extruded through the dispensing tube. The bone cement paste is thus easier to apply.

Furthermore, there can in one embodiment be provision for the volume of the monomer liquid in the ampoule to be at least as large as the volume of the air-filled spaces between the cement powder particles in the cartridge, in one embodiment at least as large as the volume of the liquid-containing pipes between the interior of the cartridge and the interior of the receptacle plus the volume between the pumping plunger and the dispensing plunger at a separation which corresponds to the length of the spacer, minus the volume of the material of the ampoule, plus the volume of the air-filled spaces between the cement powder particles in the cartridge. This ensures that sufficient monomer liquid is available to form the bone cement paste.

One embodiment is a method to produce a bone cement paste, for example, a pasty polymethyl methacrylate bone cement paste, whereby the bone cement paste is produced from a cement powder and a monomer liquid, characterised by the following steps A) an ampoule containing the monomer liquid and a spacer which extends in a longitudinal direction are arranged in a receptacle between a pumping plunger which can be moved in the longitudinal direction and a dispensing plunger, whereby the pumping plunger is pressed in the longitudinal direction towards the dispensing plunger, B) the movement of the pumping plunger towards the dispensing plunger causes an ampoule head of the ampoule to be broken open or broken off, whereby a free end of the spacer is moved inside the opened ampoule against an ampoule body of the opened ampoule so that at least a part of the wall of the ampoule body is arranged between the spacer and an inner wall of the receptacle during the movement, C) the opened ampoule is compressed and further broken by the movement of the pumping plunger towards the dispensing plunger, and the monomer liquid is thus squeezed out of the receptacle and into the cement powder, where it mixes with the cement powder to form the bone cement paste, D) the spacer is clamped between the pumping plunger and the dispensing plunger and thus prevents a further reduction of the separation of the dispensing plunger to the pumping plunger and thus a further expression of monomer liquid from the receptacle into the bone cement paste.

This provides for the method to be carried out with a device according to one embodiment.

The method thus has the advantages of the device according to one embodiment.

Furthermore, there can be provision that in Step C) the monomer liquid is pressed through at least one connection in the dispensing plunger, the connection being impermeable to the cement powder but permeable to gases and the monomer liquid, into a cartridge which contains the cement powder.

This prevents the cement powder penetrating into the connection beforehand, reacting there with the monomer liquid and thus sealing the connection so that no further monomer liquid can be pressed into the cement powder.

It can furthermore be provided that the movement of the pumping plunger in Step B) and C) is driven by an axial movement of a rod of an extrusion device which is fastened to the receptacle before Step A).

The method or the movement of the pumping plunger can thus be driven with a conventional extrusion device such as an extrusion gun.

There can also be provision for at least one cutting element with a cutting edge to be arranged on the rear of the dispensing plunger or on the front of the pumping plunger, whereby in Step C) the wall of the ampoule body is cut or broken with the cutting edge, the free end of the spacer having a separation to the at least one cutting element, in one embodiment a separation in the longitudinal direction of at least 10 mm.

This means that, as far as possible, no shards of the ampoule find their way between the free end of the spacer and the dispensing plunger or the pumping plunger. This can ensure that the separation between the pumping plunger and the dispensing plunger in Step D) can be set very accurately and thus the quantity of the monomer liquid introduced into the cement powder can be predetermined very accurately. This means that the desired consistency of the bone cement paste can be adjusted very precisely.

It is finally also proposed that the cement powder is arranged in an inner chamber of a cartridge, the dispensing plunger being arranged in the interior of the cartridge so as to be moveable in the longitudinal direction, whereby in Step C) the monomer liquid is pressed into the interior of the cartridge and whereby after Step D) in a Step E) the dispensing plunger is pressed in the longitudinal direction into the interior of the cartridge by the pumping plunger, and thus the bone cement paste is pressed out of the interior of the cartridge.

The dispensing plunger can thus be driven by the linear movement of the pumping plunger as well, and the bone cement paste can be dispensed with the same movement and thus with the same linear drive that is also used for pressing the monomer liquid into the cement powder.

There can be provision here that in Step E) a seal, for example a pore filter, in a dispensing aperture on the front of the cartridge is moved or pressed outwards by the pressure acting on the bone cement paste, the seal then in one embodiment being removed from the dispensing aperture and in one embodiment an application tube then being fastened on the front of the cartridge.

One embodiment is based on the surprising finding that the spacer that has a separation from the inner wall of the receptacle succeeds in setting the minimum separation between the pumping plunger and the dispensing plunger with such precision that the quantity of monomer liquid transferred from the receptacle into the cement powder can be set very accurately and can be reproduced well. Since a free end of the spacer can move in the interior of the ampoule body of the opened ampoule when it is squeezed, the breaking front or the cutting front which runs through the ampoule body can have a separation from the free end of the spacer such that the risk of fragments of the ampoule (that is, shards of the ampoule) getting between the free ends of the spacer and the facing front of the pumping plunger or the facing rear of the dispensing plunger is avoided (or can at least be reduced). Thus the length of the spacer in the longitudinal direction determines the separation between the dispensing plunger and the pumping plunger when the pumping plunger is pressed so far towards the dispensing plunger that the spacer is clamped between the pumping plunger and the dispensing plunger. Only the base of the ampoule is then still between the free end of the spacer and the front of the pumping plunger or the rear of the dispensing plunger, whereby this base in one embodiment shatters as well. The volume between the pumping plunger and the dispensing plunger in the compressed state is hence known very precisely. Since the volume of the spacer is known and the volume of the ampoule walls, or the shards of the ampoule, is known, the quantity of monomer liquid from the ampoule which remains in the volume can be predicted very accurately and thus the quantity of the monomer liquid pressed into the cement powder. The volume of a holder which may be present as a transport securing device for the ampoules in the receptacle is also known. It is thus possible to reproducibly produce the bone cement paste with the desired consistency with the device according to one embodiment and the method according to one embodiment by pressing a defined quantity of the monomer liquid into the cement powder.

It is advantageous in one embodiment when at least one cutting element with a cutting edge is provided which mechanically breaks open or cuts open the ampoule body at a defined point, which is as far removed as possible from the free end of the spacer. The breakage front or cutting front where the fragments or shards are produced is then as far removed from the free end of the spacer as possible.

One embodiment is also based on the fact that first the ampoule head is pressed into the cylindrical ampoule body (the glass wall) of the ampoule when the pumping plunger moves towards the dispensing plunger, or first the at least one spacer is pressed into the ampoule body. Simultaneously, the at least one spacer penetrates into the interior of the cylindrical ampoule body of the ampoule without the ampoule body being destroyed by the at least one spacer. When the pumping plunger moves further towards the dispensing plunger, the spacer and if applicable the ampoule head are pushed into the cavity of the ampoule body and, on the other hand, the front of the pumping plunger or in one embodiment the at least one cutting element on the front of the pumping plunger strikes the wall of the ampoule body (the glass wall of the glass ampoule), and acts on it. Alternatively, the rear of the dispensing plunger or in one embodiment the at least one cutting element on the rear of the dispensing plunger can act on the wall of the ampoule body. The wall starts to break when the pumping plunger moves further towards the dispensing plunger. This means that the formation of the fragments (the glass shards) takes place behind the forward movement of the spacer. The spacer then runs into the dispensing plunger or the pumping plunger and prevents the further movement of the pumping plunger towards the dispensing plunger. This process can only be carried out with precision because the formation of the glass shards takes place behind the advancing free end of the spacer. It is therefore impossible for shards to move between the spacer and the dispensing plunger or pumping plunger.

According to one embodiment, when the spacer is realized with several rods, the spacer in one embodiment slips off outwards at the base of the ampoule towards the cartridge wall shortly before the spacer runs into the plunger. This means that when the spacer moves the pumping plunger further forwards, the dispensing plunger is synchronously moved together with it towards the cartridge head without the separation between the dispensing plunger and the pumping plunger being able to change. This means that the axial length of the spacer (in the longitudinal direction) unambiguously defines the separation between the dispensing plunger and the pumping plunger. The prerequisite for this is that the spacer is designed to be mechanically stable, particularly to be resistant to torsion and buckling. An elastic deformation of the spacer can be provided for, however.

The device according to one embodiment with cement powder in the interior of the cartridge has the advantages that the two starting components of the bone cement paste are stored in the closed cementing system and that the mixing of the starting components is carried out in the closed device. This means that the device does not have to be filled by the user. It is then a full pre-packed cementing system. The medical user does not come into contact at all with the individual starting components of the bone cement. Offensive smells are therefore only minimal.

An advantage of the device according to one embodiment also consists in the fact that the monomer liquid is pressed into the cement powder by the simple forward movements of a rod of a manually driven extrusion device. The air present between the particles of cement powder is thereby replaced by the monomer liquid. A homogeneous bone cement paste is produced without the need for manual mixing with mixing rods with mixing paddles. This means that error-prone manual mixing is no longer necessary. The operation of the device is as simple as possible. It is a ready-to-use system.

The advantages of devices and methods according to one embodiment are also based on the fact that the linear forward movement of rods of manually operated extrusion devices, which is known as such, can be used such that first a monomer liquid container is opened by the continuous action of the force of the linear forward movement of the rod, the monomer liquid container then being compressed, which causes the monomer liquid to be discharged from the monomer liquid container and be pressed into a compacted cement powder, the air present between the cement powder particles being displaced by the pressed-in monomer liquid and a bone cement paste being formed after the monomer liquid has wet the particles of cement powder. The precondition for this is the use of a cement powder which is adjusted such that it is wetted very well by the monomer liquid and can draw it in by virtue of the capillary effect.

The device can be used as a hygienic disposable product, since it can be largely manufactured from plastic and because all parts including the interiors and the cement powder can be sterilised with the aid of ethylene oxide.

An exemplary device according to one embodiment for the storage, mixing and dispensing of polymethyl methacrylate bone cement can for example include:

a cartridge in the form of a hollow cylinder; an axially moveable pumping plunger; an axially moveable dispensing plunger which is permeable to gases or liquids but impermeable to powder particles; a first cavity with a glass ampoule arranged therein which contains a monomer liquid; a second cavity with cement powder arranged therein and also an axially moveable sealing plug which is permeable to gases but impermeable to powder particles; at least one wedge-shaped cutting element which is arranged radially such that the glass wall of the glass ampoule lies on the same radius relative to the longitudinal axis of the cartridge; at least one spacer which extends parallel to the longitudinal axis of the cartridge between the dispensing plunger and the pumping plunger, whereby the spacer surrounds an ampoule head of the glass ampoule and is arranged on a radius which is smaller than the radius of the interior of the glass wall of the glass ampoule, the spacer having an axial separation between the dispensing plunger and pumping plunger (in the longitudinal direction) such that the volume of the first cavity, which is formed by the pumping plunger, the dispensing plunger which is permeable to gases and liquids and impermeable to powder particles, and the inner wall of the cartridge, is greater than or equal to the volume of the glass shards of the burst glass ampoule.

The spacer and the cutting element can be arranged either together on the dispensing plunger or both alternatively on the pumping plunger.

It is furthermore possible to arrange the at least one spacer and in one embodiment also the at least one cutting element on a ring or in a ring, and to arrange this in front of the pumping plunger or behind the dispensing plunger.

Provision can be made for the spacer to include several rods, which are fastened on the rear of the dispensing plunger or on the front of the pumping plunger and extend into the receptacle in the longitudinal direction. There can be provision here for the rods to be additionally connected with each other via at least one ring, the at least one ring being separated from the rear of the dispensing plunger or the front of the pumping plunger. The rods are thus stabilised and stabilise each other. A normal (not reinforced) synthetic material can thus be used for the rods, since the rods stabilise each other via the at least one ring. The rods and the at least one ring are in one embodiment manufactured in one piece from a synthetic material.

According to one embodiment, there can be provision for the spacer and the at least one cutting element to be arranged on the pumping plunger, on the front of the pumping plunger which is facing the dispensing plunger when the ampoule with the ampoule head is pointing towards the pumping plunger.

A further provision according to one embodiment can be that the spacer and the at least one cutting element are arranged on the dispensing plunger which is permeable to gases and liquids and impermeable to powder particles, on the rear of the dispensing plunger which is facing towards the pumping plunger, when the ampoule with the ampoule head is pointing towards the dispensing plunger.

The spacer is in one embodiment formed by three or four rods, whereby the rods are round, triangular, rectangular or T-shaped. The rods can have the form of hollow bodies or solid bodies. The rods can consist of synthetic materials, polyamide, polyketone, polyether sulphone and polyimides and in one embodiment of glass-fibre reinforced plastics. Additionally, it is also possible for the rods to consist of steel, titanium and titanium alloys.

One embodiment provide for the spacer to be formed by a hollow cylinder or parts of a hollow cylinder.

The spacer is in one embodiment at least five times as high as the cutting element in the axial direction. This ensures that the formation of the glass shards always takes place behind the free end of the spacer.

It is preferable in one embodiment for all cutting elements of the at least one cutting element to extend a maximum of 2 mm from the front of the pumping plunger or the rear of the dispensing plunger, in one embodiment a maximum of 1 mm.

Figure 5:
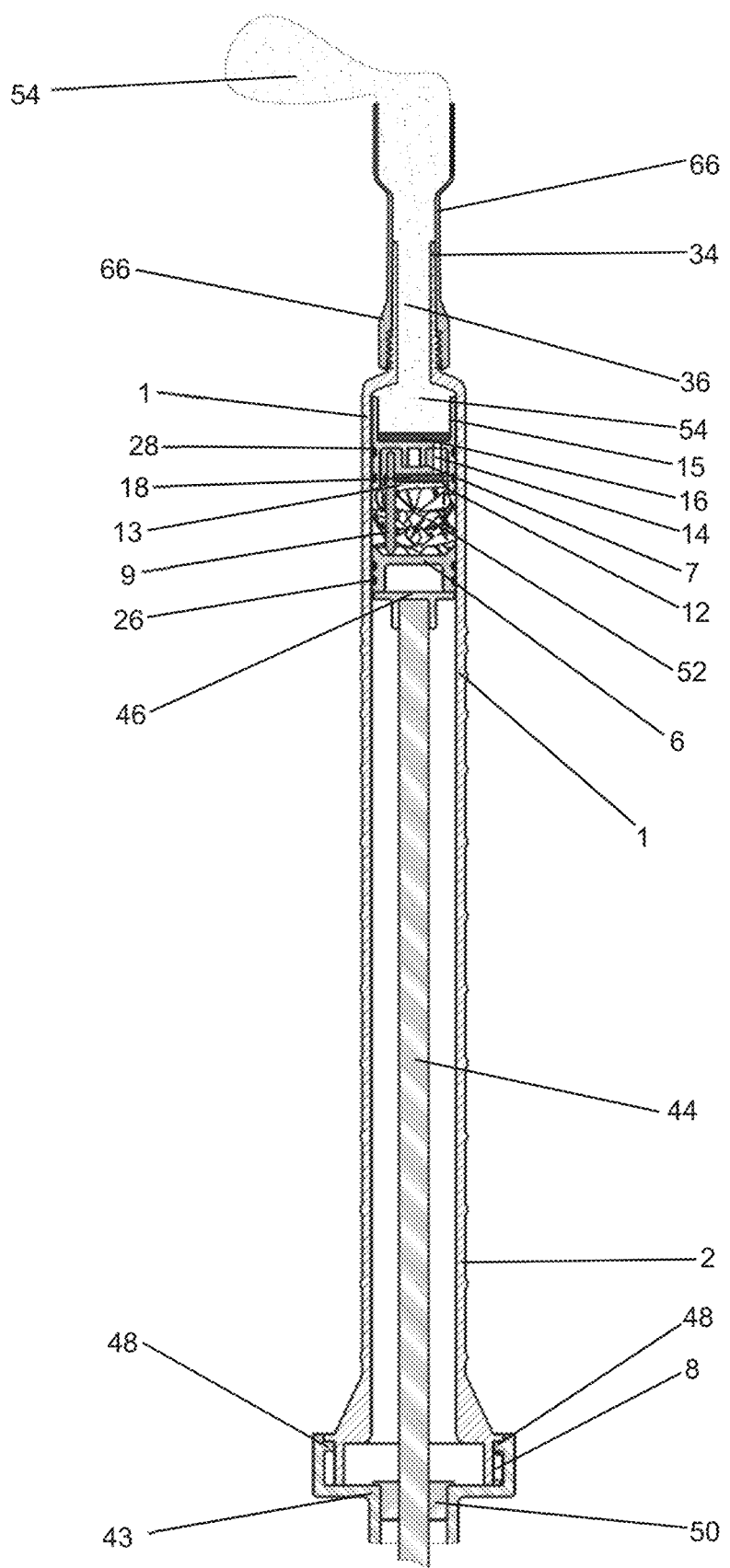
FIG. 5: illustrates a schematic cross-sectional view of the first device according to one embodiment as per FIGS. 1 to 4 after the bone cement paste produced has been extruded.
Figure 6:
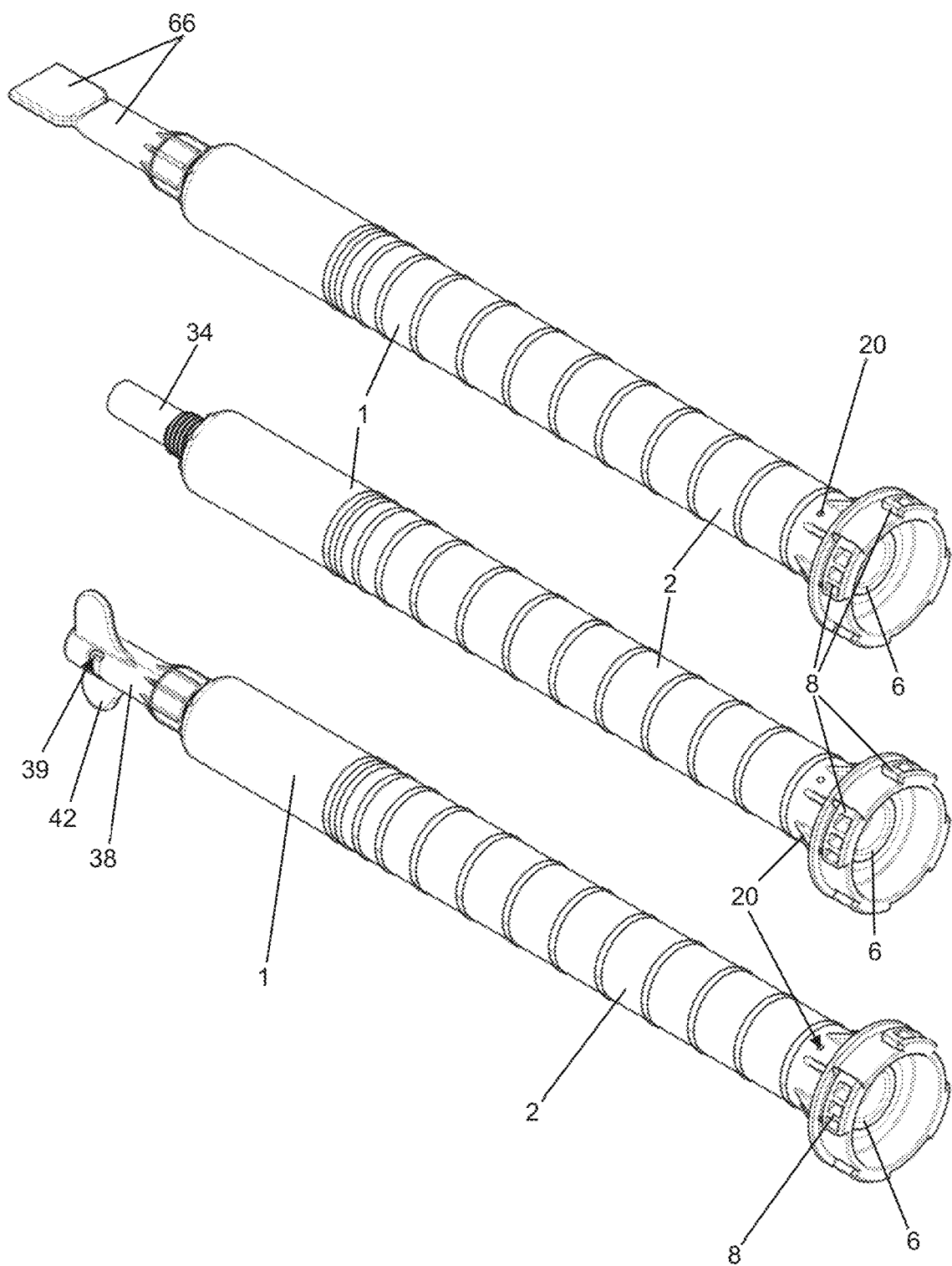
FIG. 6: illustrates three schematic perspective views of devices according to one embodiment as per FIGS. 1 to 5 with applicator tube, without an attachment, and with a cap on the dispensing tube.
Figure 7:
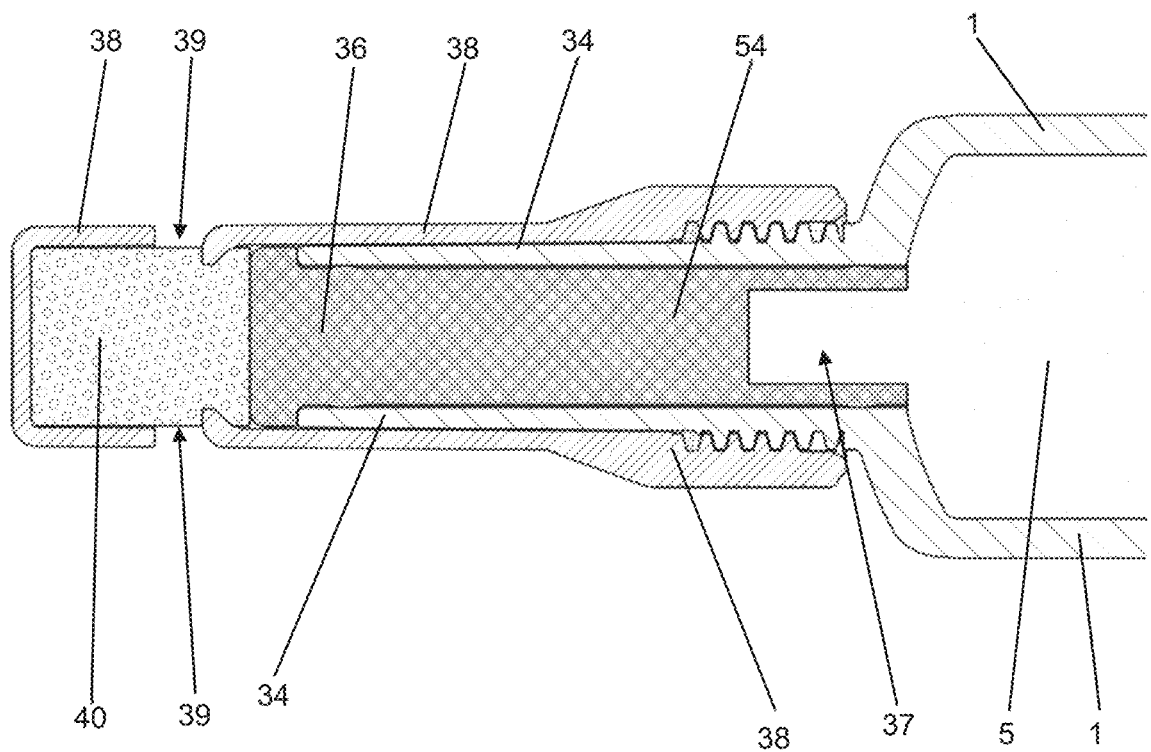
FIG. 7: illustrates a schematic cross-sectional view as a section enlargement through the front part of the first device according to one embodiment as per FIG. 1 in the starting state.
Figure 8:
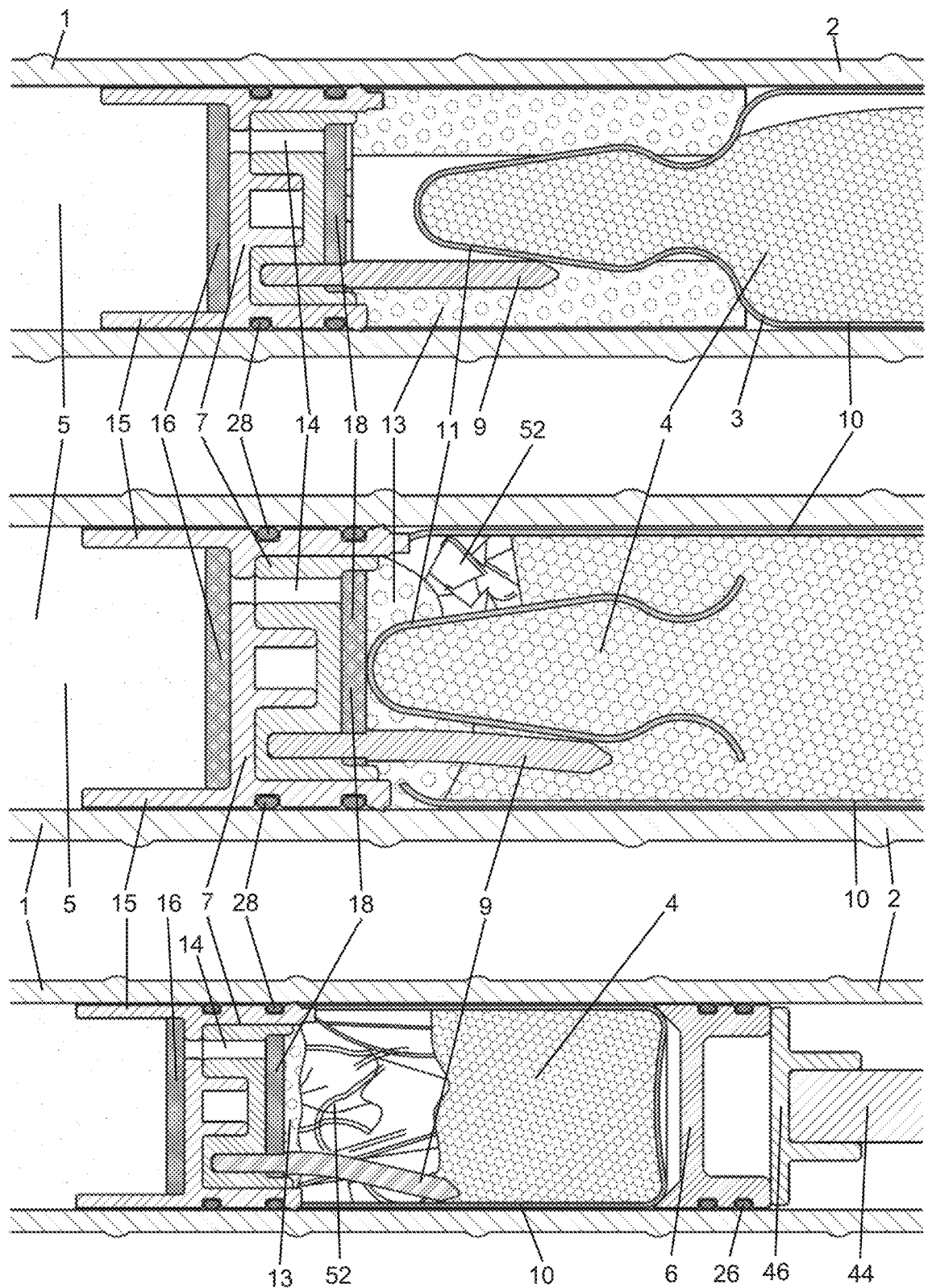
FIG. 8: illustrates three schematic cross-sectional views as section enlargements of the first device according to one embodiment as per FIGS. 1 to 7 in the starting state, after the ampoule has been broken open and as the ampoule is being broken, as depicted in the first, the third and the fourth illustrations from the top in FIG. 3.
Figure 9:
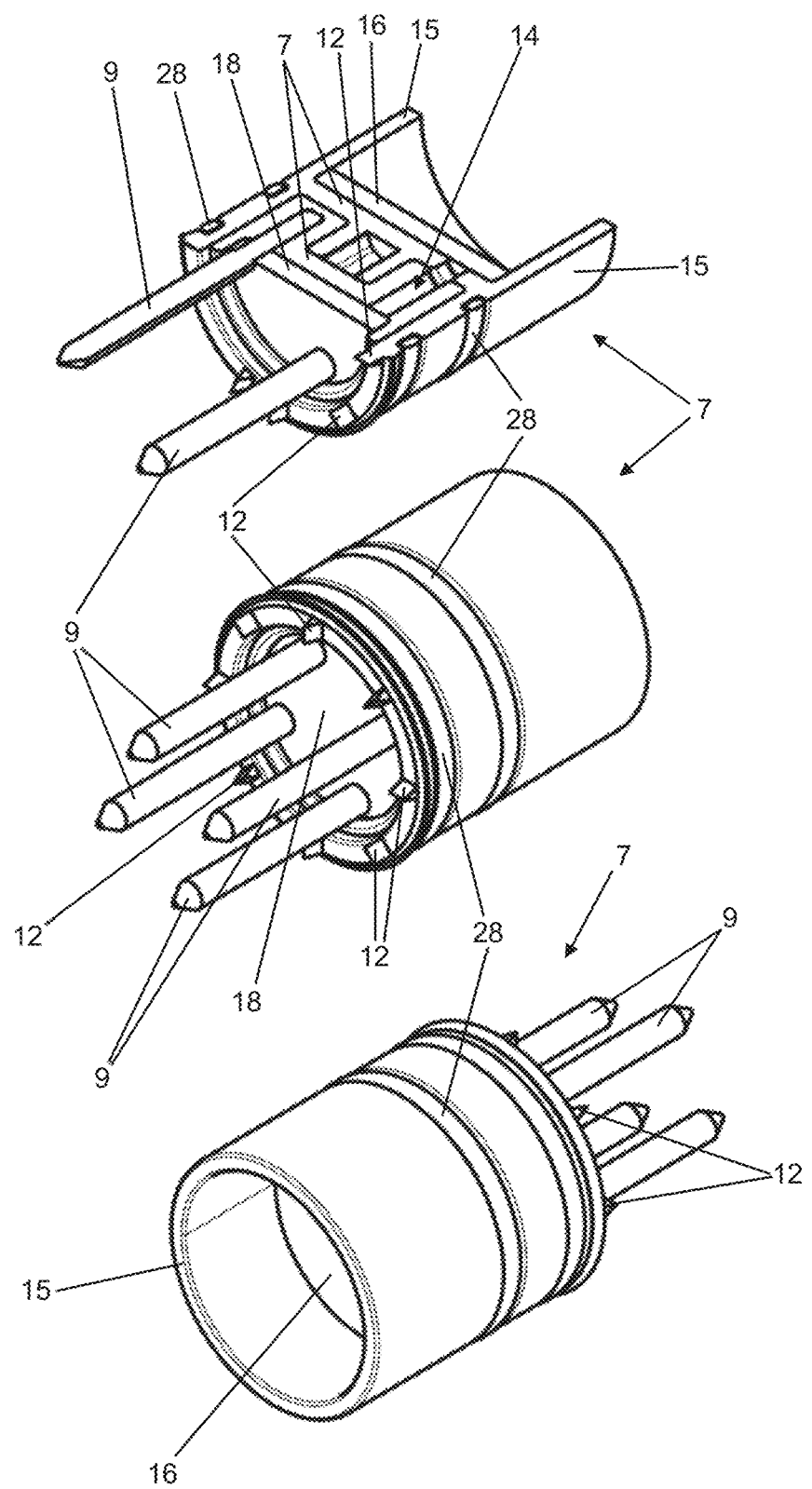
FIG. 9: illustrates a perspective cross-sectional view (top) and two further perspective views (centre and bottom) of the dispensing plunger of the first device according to one embodiment as per FIGS. 1 to 8.

The FIGS. 1 to 9 depict illustrations of a first device according to one embodiment to store and mix a bone cement paste. The FIGS. 1 to 6 depict different schematic overall views of the first exemplary device according to one embodiment. FIGS. 7 and 8 depict section enlargements of schematic cross-sectional views as detailed views of different regions of the first device according to one embodiment, and FIG. 9 illustrates three schematic detailed views of a dispensing plunger of the first device according to one embodiment.

Figure 2:
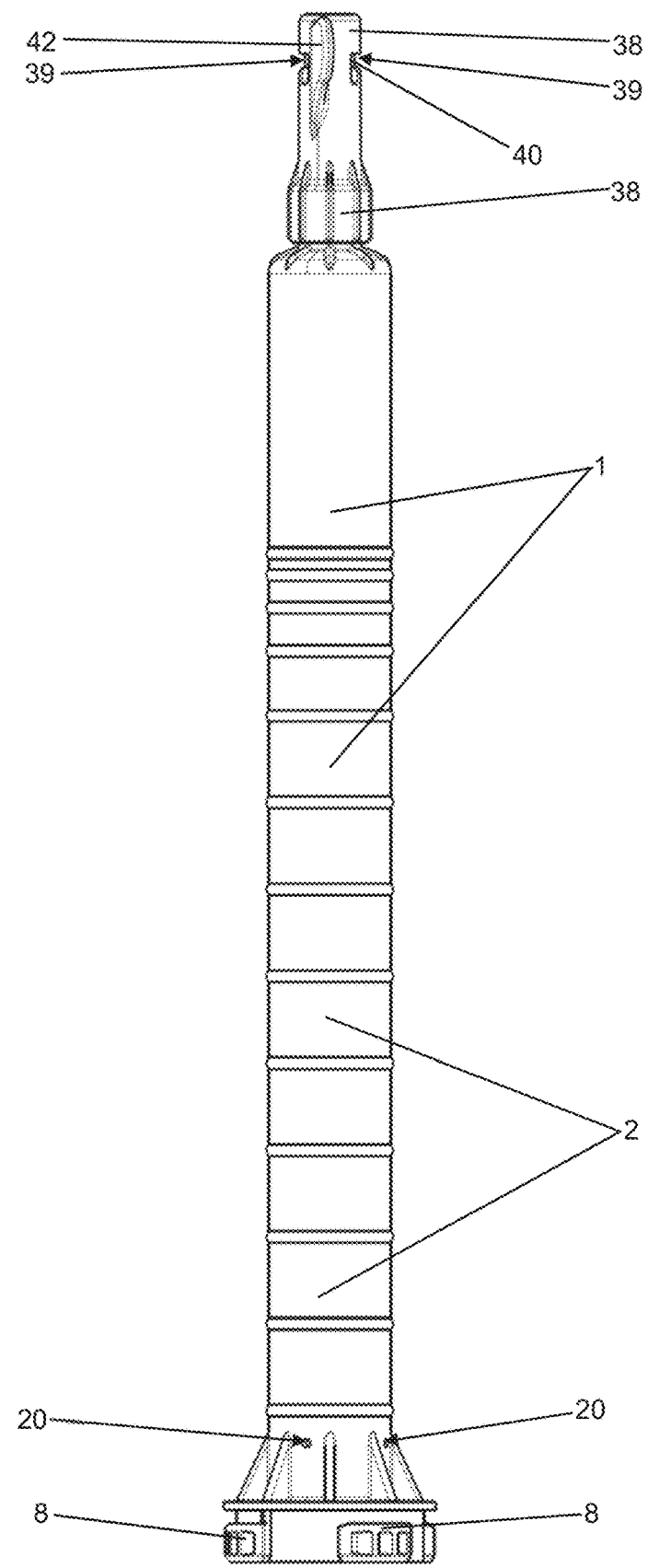
FIG. 2: illustrates a schematic side view of the first device according to one embodiment as per FIG. 1.

The first device according to one embodiment consists mainly of a tubular plastic container, which forms a cartridge 1 with a cylindrical interior as the front part (in FIGS. 1, 2 and 5 at the top, in FIG. 3 at the bottom left, in FIGS. 4, 7 and 8 on the left, and in FIG. 6 at the top left-hand side) and which forms a receptacle 2 with a cylindrical interior for a glass ampoule 3 (or a plastic ampoule 3) as the container for a monomer liquid 4 as the rear part. The rear of the device is illustrated in FIGS. 1, 2 and 5 at the bottom, in FIG. 3 at the top right, in FIG. 4 on the right and in FIG. 6 at the bottom right. The tubular shape of the container can be recognised particularly well in the cross-sectional views of FIGS. 1, 3 and 5. The interior of cartridge 1 as well as the interior of receptacle 2 are cylindrical with a circular base. The diameters of the interior of cartridge 1 and the diameter of the interior of receptacle 2 are of equal size and flush with each other. The container with the receptacle 2 and the cartridge 1 is in one embodiment made of plastic by injection moulding. Receptacle 2 thus has a cylindrical interior into which the glass ampoule 3 is inserted. The monomer liquid 4 is contained in the glass ampoule 3. A cement powder 5 is filled or in one embodiment pressed into the interior of cartridge 1. The monomer liquid 4 and the cement powder 5 form the starting components for a PMMA bone cement, which can be produced with the device. The glass ampoule 3 allows the monomer liquid 4 to be stored for a very long time in the receptacle 2 and thus in the device. The cement powder 5 can also be stored in the device over longer periods of time. The device is therefore suitable for the storage of the monomer liquid 4 and the cement powder 5 as starting components of a bone cement paste of PMMA bone cement. The device is also suitable for and provides for the mixing of the bone cement paste from the starting components and the dispensing of the mixed bone cement paste as well, however.

A pumping plunger 6 made of synthetic material which can move in the longitudinal direction in the cylindrical interior of the receptacle 2 is arranged in the receptacle 2. The pumping plunger 6 is arranged close to the rear of the receptacle 2. The glass ampoule 3 can be compressed with the pumping plunger 6 in the receptacle 2 and thus be shattered by pressing the pumping plunger 6 towards the front, that is, in the direction of cartridge 1. The pumping plunger 6 has skimmers at the front with which shards of the glass ampoule 3 are skimmed off the inner wall of the receptacle 2. To this end, the skimmers come into contact with the side of the inner wall of the interior of the receptacle.

A dispensing plunger 7 made of synthetic material is arranged in the interior of the cartridge 1 at its rear (in the FIGS. 1 and 2 downwards, in FIG. 3 towards the top right, in FIGS. 4 and 8 towards the right), the plunger being depicted in detail in the illustrations after FIG. 9. A means of fastening 8 is provided at the rear of the receptacle 2, with which the receptacle 2 can be connected to an extrusion device 43 (not visible in FIGS. 1 to 3, but see FIGS. 4 and 5). The means of fastening 8 is in one embodiment suitable for and provided to form a bayonet coupling 8. This allows the pumping plunger 6, which is freely accessible from the rear of the receptacle 2, to be driven forwards with the extrusion device 43 towards the front of the cartridge 1.

The dispensing plunger 7 has on its rear four rods 9 as spacers which determine the separation between the dispensing plunger 7 and the pumping plunger 6 when the pumping plunger 6 is pushed fully towards the dispensing plunger 7 (see FIG. 5). The rods 9 are rotationally symmetric (for example cylindrical), but can also have a rectangular cross-section. The rods 9 extend at least 10 mm from the rear of the dispensing plunger 7 into the receptacle 2. The rods 9 taper towards the pumping plunger 6, the tips having a blunt end (see FIG. 9). The tapered tips of the rods 9 mean it is easier to push the shards 52, which are produced between the tips of the rods 9 and the pumping plunger 6 when the glass ampoule 3 is crushed by the movement of the pumping plunger 6, past the sides of the rods 9. The blunt end of the rods 9 prevents the rods 9 from being pressed into the pumping plunger 6 or the rods 9 being deformed at the tip, and thus the length of the rods 9 changing, and hence the separation between the dispensing plunger 7 and the pumping plunger 6, and thus the space in between varying and becoming less predictable. This means that the quantity of monomer liquid 4 which remains in the space between the dispensing plunger 7 and the pumping plunger 6 after the extrusion (see FIG. 5) and thus the quantity of monomer liquid 4 pressed into the cement powder 5 is known very precisely and is predictable. The consistency of the bone cement paste 54 produced can thus be adjusted and reproduced very accurately.

The glass ampoule 3 has an ampoule body 10 and an ampoule head 11 which are connected with each other via a thin neck. The glass ampoule 3 can be opened very simply by breaking off the ampoule head 11 of the ampoule body 10. The rods 9 run laterally from the ampoule head 11 and surround it (see FIGS. 1, 3 and 4) so that the rods 9 pass the ampoule head 11 at the side when the glass ampoule 3 moves because the pumping plunger 6 is being driven forward, and are driven into the shoulders of the glass ampoule 3 into the ampoule body 10 (see FIGS. 4 and 8). The rods 9 can be deformed elastically and are manufactured from a synthetic material. The elastic deformability allows fragments of the glass ampoule 3 to be guided more easily past the rods 9. The rods 9 are separated at least so far from the inner wall of the receptacle 2 that the wall of the ampoule body 10 fits between the rods 9 and the inner wall of the receptacle 2. The rods 9 thus run in the interior of the ampoule body 10 when the pumping plunger 6 is driven forwards. There can be provision for the rods 9 to be connected with each other via a shared ring (not illustrated). The ring is arranged parallel to the rear of the dispensing plunger 7 and can be separated from the rear of the dispensing plunger 7 by half the length of the rods 9, for example. The rods 9 are thus stabilised and do not buckle as easily. The longer the rods 9, the more advantageous is a stabilisation with a ring (or several rings as well). The inner diameter of the ring here must be large enough to be able to accept the ampoule head 11.

Eight wedge-shaped cutting elements 12, which are provided for cutting or breaking the ampoule body 10 of the glass ampoule 3 when the pumping plunger 6 is driven forwards, are arranged on the rear of the dispensing plunger 7. The edges of the cutting elements 12 run radially outwards and are arranged on the outside of the dispensing plunger 7 so that the edges of the cutting elements 12 can run through the whole wall of the ampoule body 10 and thus cause it to shatter. The tips of the rods 9 are separated from the cutting elements 12 in the longitudinal direction of the device so that the breaking front on which the ampoule body 10 is crushed is separated from the tips of the rods 9. This prevents large quantities of shards 52 being produced between the tips of the rods 9 and the pumping plunger 6, which could be trapped between the tips of the rods 9 and the pumping plunger 6 and thus have an impact on the minimum volume between the pumping plunger 6 and the dispensing plunger 7 and hence the quantity of monomer liquid 4 pressed into the cement powder 5.

A holder 13 in the form of a sleeve of foam material is provided for impact protection for the stable storage of the glass ampoule 3. The sleeve-shaped holder 13 surrounds the ampoule head 11 and is inserted between the rods 9 and the inner wall of the receptacle 2. The holder 13 is permeable to the monomer liquid 4 and manufactured from a synthetic material.

The cartridge 1 and the receptacle 2 are designed in one piece as a combined part made of synthetic material. For the monomer liquid 4, the receptacle 2 and the cartridge 1 are connected so as to be permeable to liquids via a connection 14 in the dispensing plunger 7. A hollow cylinder 15 is arranged on the front of the dispensing plunger 7. The connection 14 through the dispensing plunger 7 opens through a pore filter 16, which is impermeable to the cement powder 5 but permeable to the monomer liquid 4, into the interior of the cartridge 1.

Where the connection 14 joins, a filter 18 is arranged in the dispensing plunger 7 with which the shards 52 of the glass ampoule 3 can be retained. A sieve can be provided instead of the filter 18 or in addition to the filter 18.

Several ventilation apertures 20 are provided in the wall of the receptacle 2 through which the interior of the receptacle 2 can be sterilised with the aid of a sterilising gas such as ethylene oxide. The ventilation apertures 20 are arranged in the immediate vicinity of the pumping plunger 6 so that the pumping plunger 6 slides directly in front of the ventilation apertures 20 and thus seals the ventilation apertures 20 directly when the pumping plunger 6 is driven forwards towards the cartridge 1. This prevents monomer liquid 4 from escaping through the ventilation apertures 20 when the glass ampoule 3 in the receptacle 2 is opened.

The cylindrical pumping plunger 6 has an external circumference matching the cylinder geometry of the interior of the receptacle 2 and is sealed via two circumferential seals 26 against the inner wall of receptacle 2 so as to be liquid tight. The dispensing plunger 7 is also sealed via two circumferential seals 28 against the inner wall of cartridge 1 so as to be liquid tight. These seals 26, 28 serve to prevent monomer liquid 4 or bone cement paste 54 escaping and hence to prevent the environment (the operating theatre and the user) from being contaminated. The seals 26, 28 can consist of rubber for this purpose.

The interior of the cartridge 1 opens at the front into a dispensing tube 34, which restricts a front dispensing aperture of the cartridge 1. The dispensing tube 34 has an external thread at its base. In the inside of the dispensing tube 34, a pore filter 36 is arranged as a seal for the cartridge 1. The pore filter 36 is impermeable to the cement powder 5 but permeable to gases. A recess 37 is provided in the rear of the pore filter 36. The cement powder 5 is also contained in the recess 37. A cap 38 is fastened on the external thread of the dispensing tube 34, the front part of the cap 38 being filled with polystyrene or plastic foam. Two wings 42 are provided on the cap 38 so that the cap 38 can easily be screwed off the dispensing tube 34 like a wing nut. The cap 38 has lateral apertures 39. This design allows the interior of the cartridge 1 and the cement powder 5 to be sterilised with the aid of ethylene oxide since the apertures 39 in the cap 38, the polystyrene or the plastic foam 40, the pore filter 36 and the spaces between the powder particles of the cement powder 5 are permeable to air. At the same time, air can be pressed out of the receptacle 2 through the cement powder 5, the pore filter 36, the polystyrene or the plastic foam 40, and the apertures 39 in the cap 38, when the pumping plunger 6 is pressed towards receptacle 1. The cap 38 together with the polystyrene or plastic foam 40 and with the pore filter 36 forms a seal for the dispensing aperture of the cartridge 1 or for the dispensing tube 34.

The cement powder 5 is enclosed in the cartridge 1 since all apertures 39 and connections 14 are sealed with the aid of the pore filters 16, 36 so as to be impermeable to the cement powder 5. The contents of the cartridge 1 can be sterilised by evacuation and rinsing with ethylene oxide. This means the device is also suitable for the long-term storage of the cement powder 5.

Figure 3:
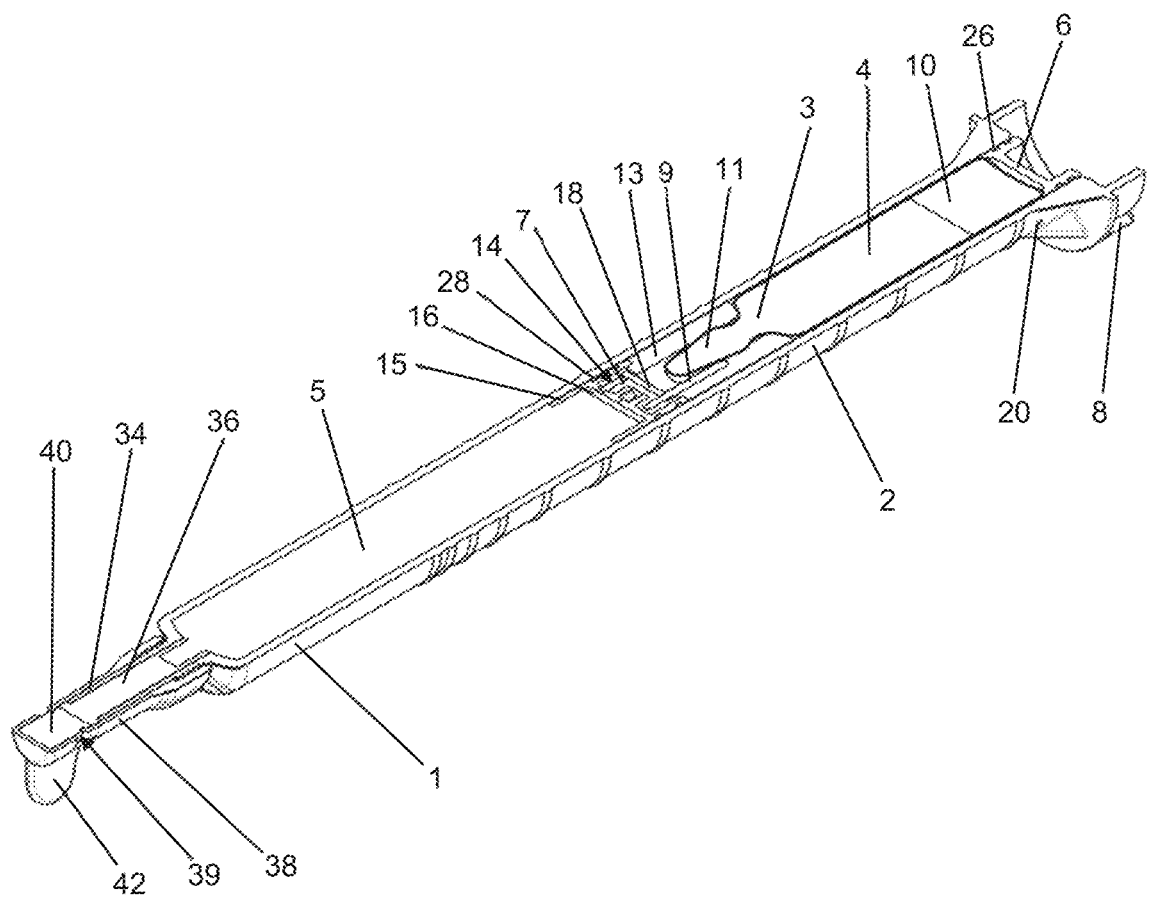
FIG. 3: illustrates a schematic perspective cross-sectional view of the first device according to one embodiment as per FIGS. 1 and 2.
Figure 4:
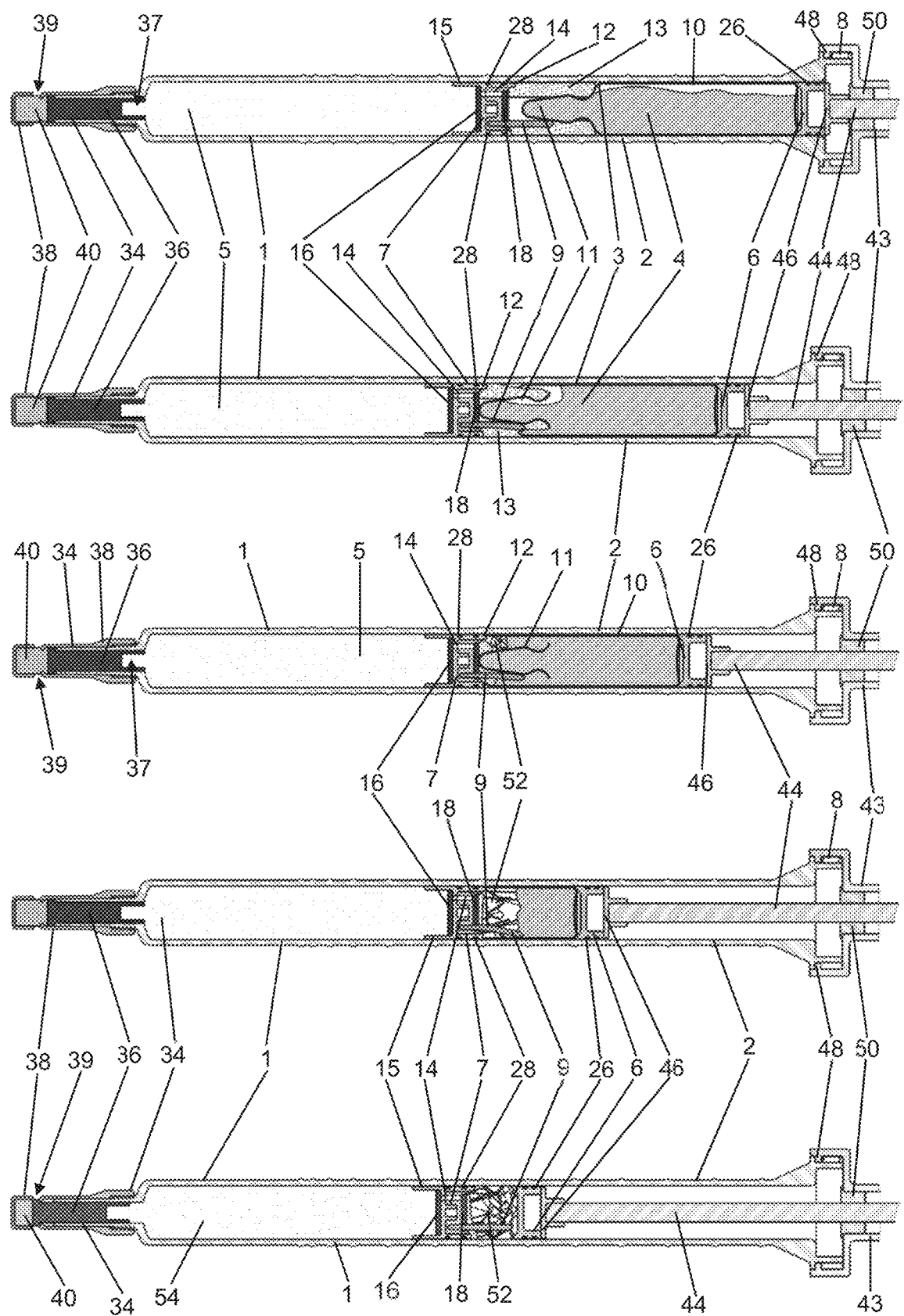
FIG. 4: illustrates five schematic cross-sectional views of the first device according to one embodiment as per FIGS. 1 to 3 with an extrusion device connected, one above the other, to illustrate the sequence of a method according to one embodiment.

FIG. 4 illustrates five schematic cross-sectional views of the first device according to one embodiment as per FIGS. 1 to 9, one above the other, to illustrate the sequence of a method according to one embodiment. The state in FIG. 5 is finally reached as the last step of the method. In this context, FIG. 7 illustrates a section enlargement of the top illustration of FIG. 4, and the three illustrations of FIG. 8 illustrate section enlargements of the first illustration, the third illustration and the fourth illustration from the top in FIG. 4.

At the start of the method, the device is in the starting state, as is illustrated in FIGS. 1 to 3 as well. In this state, the device is inserted into an extrusion device 43 according to one embodiment which essentially corresponds to a conventional cartridge gun. This situation is illustrated in the top illustration of FIG. 4. The extrusion device 43 has a rod 44 which can be driven forwards linearly. Only the front part of the extrusion device 43 is illustrated. The extrusion device 43 also includes a handle and a toggle lever (not illustrated in the illustrations) to drive the rod 44 of the extrusion device 43 manually, as happens with conventional manually driven extrusion devices 43 as well. The device is fastened to the extrusion device 43 with the means of fastening 8 (see top illustration in FIG. 4). A flat plate 46 is provided at the tip of the rod 44 to drive the pumping plunger 6. The rod 44 presses the plate 46 against the pumping plunger 6 when the rod 44 is pressed into the receptacle 2 by the extrusion device 43. To this end, the extrusion device 43 is connected to the rear of the receptacle 2 via a counter-fastening means 48 so that the plate 46 presses onto the pumping plunger 6 when the rod 44 is driven forwards and drives it towards the cartridge 1. The rod 44 is mounted against a bearing 50 and above it against the counter-fastening means 48 and thus against the receptacle 2 so as to be linearly moveable.

The extrusion device 43 is operated and thereby the rod 44, and with the rod 44 the pumping plunger 6 is driven forwards in the direction of the cartridge 1. Since the rear of the glass ampoule 3 is in contact with the pumping plunger 6, the glass ampoule 3 is driven towards the dispensing plunger 7 by the pumping plunger 6. The rods 9 run past the side of the ampoule head 11 in this process. At the same time, the interior of the receptacle 2 is reduced in size and the glass ampoule 3 breaks after the ampoule head 11 is pressed against the dispensing plunger 7. In this process, the ampoule head 11 of the ampoule body 10 breaks off and is pressed into the ampoule body 10 guided by the rods 9. The monomer liquid 4 discharges from the glass ampoule 3 into the interior of the receptacle 2. The dispensing plunger 7 cannot be pushed or cannot be pushed far in the direction of the pore filter 36 by the glass ampoule 3 when the cement powder 5 is dry, that is, is not wetted by the monomer liquid 4, since the dry cement powder is not free-flowing and blocks any movement of the dispensing plunger 7. This situation is illustrated in the second illustration from the top in FIG. 4. Residual air from the receptacle 2 is expelled from the device through the filter 18, the connection 14, the pore filter 16, through the spaces between the particles of the cement powder 5, through the pore filter 36, through the plastic foam 40 and from the apertures 39 in cap 38.

As the pumping plunger 6 is driven further forwards, the rods 9 glide into the ampoule body 10. Simultaneously, the space between the pumping plunger 6 and the dispensing plunger 7 is reduced further, expelling air from the space in the process. When the air has been expelled completely, the monomer liquid 4 released is pressed out of the receptacle 2 into the interior of the cartridge 1 and thus into the cement powder 5. The monomer liquid 4 can now flow along the hollow cylinder 15 deep into the cement powder 5. The wall of the ampoule body 10 now meets the cutting elements 12 (see FIG. 4 third illustration from the top and FIG. 8 centre illustration) and is thus shattered at the cutting elements 12 as the pumping plunger 6 and the ampoule body 10 are driven further forwards. The shards 52 are thus produced at a distance from the tips of the rods 9. The shards 52 collect between the tips of the rods 9 and the rear of the dispensing plunger 7 or the filter 18 of the dispensing plunger 7. This situation is illustrated in FIG. 4, fourth illustration from the top, and bottom illustration in FIG. 8.

Only small shards 52 of the glass ampoule 3 ultimately remain, and are kept back by the filter 18 and remain in the tubular container which forms the cartridge 1 and the receptacle 2. The monomer liquid 4 is pressed into the cement powder 5 through the filter 18, the connection 14 and the pore filter 16, where it starts to react with the cement powder 5 so that the bone cement paste 54 forms from the mixture (see FIG. 4 bottom illustration). The quantity of monomer liquid 4 is chosen such that the cement powder 5 is wetted with the monomer liquid 4 right into the furthest tip of the cartridge 1, that is, right into the recess 37 in the pore filter 36. This situation is illustrated in FIG. 4, bottom drawing. As soon as the mixture is produced, the pore filter 36 is driven forwards by the pressure acting on the bone cement paste 54 caused by the pressure on the dispensing plunger 7, and compresses the plastic foam 40. When the pore filter 36 now slides forwards, it becomes visible to the user from the outside through the aperture 39 in the cap 38. This situation can be seen in FIG. 4, bottom drawing. To this end, the pore filter 36 in one embodiment has a different colour and/or brightness to the plastic foam 40. The plastic foam 40 can be white, for example, and the pore filter 36 orange.

In this state, the cap 38 with the pore filter 36 and the plastic foam 40 is unscrewed and a dispensing aperture extension in the form of an applicator tube 66 is screwed onto the dispensing tube 34 (see FIGS. 5 and 6). When the cap 38 is unscrewed, the part of the bone cement paste 54 at the very front, which is located in the recess 37 of the pore filter 38, is removed with the cap 38 and the pore filter 36. A part of the bone cement paste 54 which is potentially not mixed as well as the rest is thus removed, thus making the available bone cement paste 54 more homogeneous.

Driving the rod 44 further forwards presses the pumping plunger 6 against the rods 9, which sets the minimum distance between the pumping plunger 6 and the dispensing plunger 7, or their length in the longitudinal direction of the device determines the separation between the pumping plunger 6 and the dispensing plunger 7 and thus the volume enclosed in between. Driving the rods 44 forwards even more also drives forward the pumping plunger 6, the shards 52 and the dispensing plunger 7 arranged in front of the pumping plunger 6 and separated by the rods 9. The bone cement paste 54 is then dispensed from the cartridge 1 via the applicator tube 66. To this end, the dispensing plunger 7 is driven forwards with the rod 44 towards the dispensing tube 34 (see FIG. 5). The bone cement paste 54 from the inside of the cartridge 1 is expelled through the dispensing tube 34 and applicator tube 66 and can be applied there or used for further processing.

Finally, the hollow cylinder 15 meets the front inside of the interior of the cartridge 1. The hollow cylinder 15 here encloses a volume of bone cement paste 54 which is closest to the dispensing plunger 7. This bone cement paste 54 is retained in the device. Owing to the forces arising at the end of the extrusion process in the interior of the device, a post-densification can take place and thus a slight change in the consistency of the bone cement paste 54, which causes it to be retained in the cartridge 1. The hollow cylinder 15 produces a dead volume in the interior of the cartridge 1 which cannot be expelled from the cartridge 1 through the dispensing aperture and the dispensing tube 34. This dead volume now contains the portion of the bone cement paste 54 which possibly contains too large a proportion of monomer liquid 4. This design ensures that no bone cement paste 54 with a changing consistency due to a changing composition can be applied with the device.

The apertures 39 also act as visual markers which can be used to ascertain when the device is ready for use. When the pore filter 36 is pushed forwards because of the pressure of the bone cement paste 54 and thus compresses the polystyrene 40 in the cap 38, the pore filter becomes visible through the apertures 39. The user can thus see that the bone cement paste 54 is now fully mixed in the cartridge 1 and is thus ready for use. At this time, the user can unscrew the cap 38 with the pore filter 36 and screw the applicator tube 66 onto the dispensing tube 34. The dispensing plunger 7 can then be driven via the pumping plunger 6 with the rod 44 and thus the bone cement paste 54 can be extruded out of the cartridge 1 through the applicator tube 66.

Figure 10:
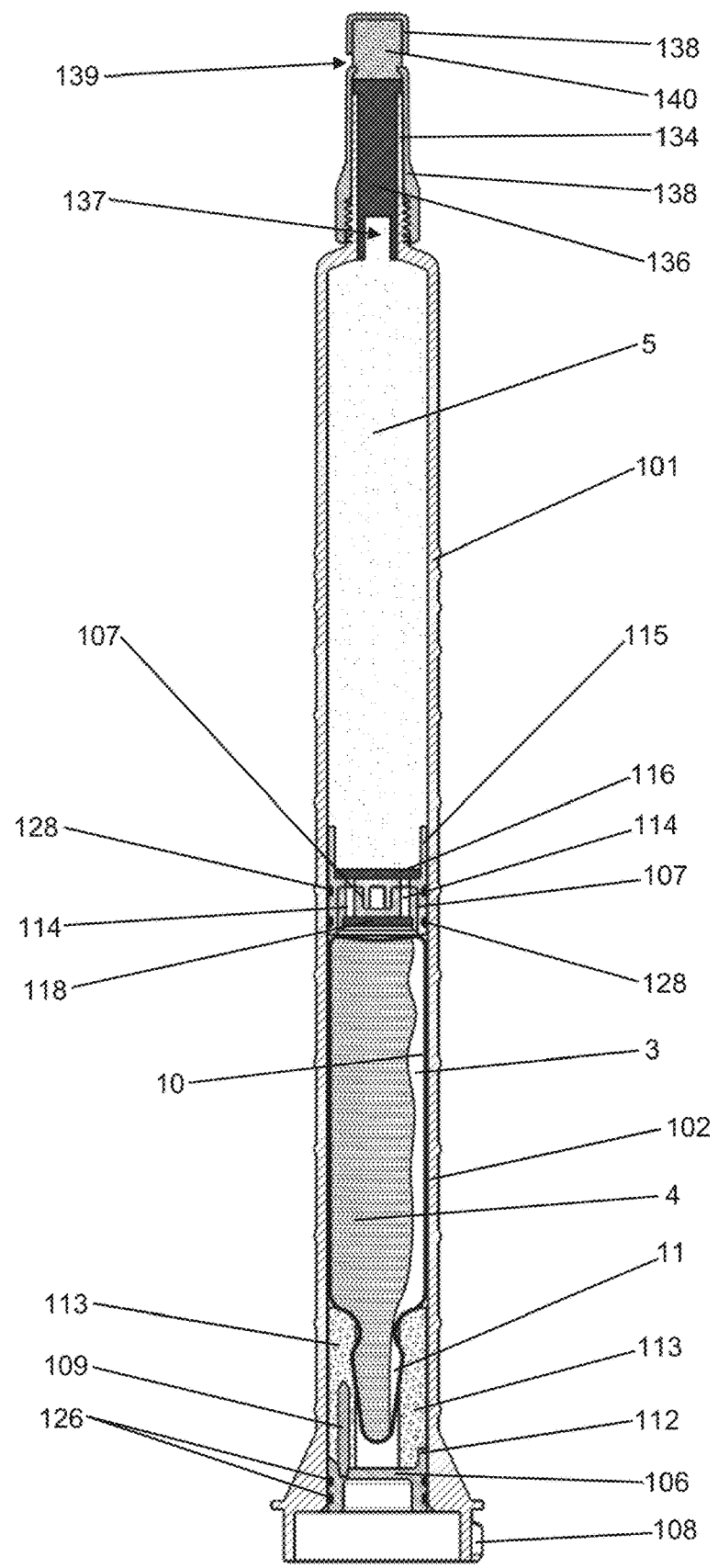
FIG. 10: illustrates a schematic cross-sectional view of an exemplary second device according to one embodiment to produce a bone cement paste.
Figure 11:
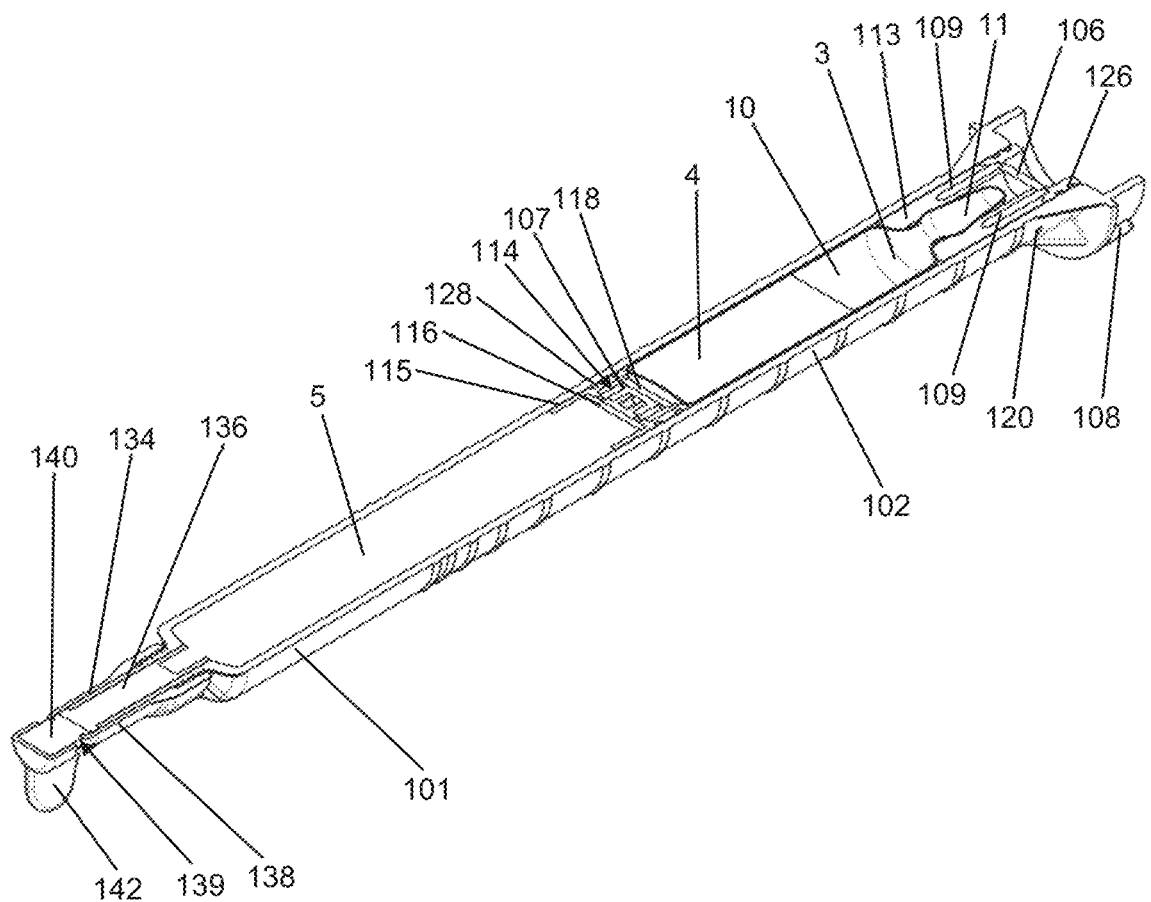
FIG. 11: illustrates a schematic perspective cross-sectional view of the second device according to one embodiment as per FIG. 10.
Figure 12:
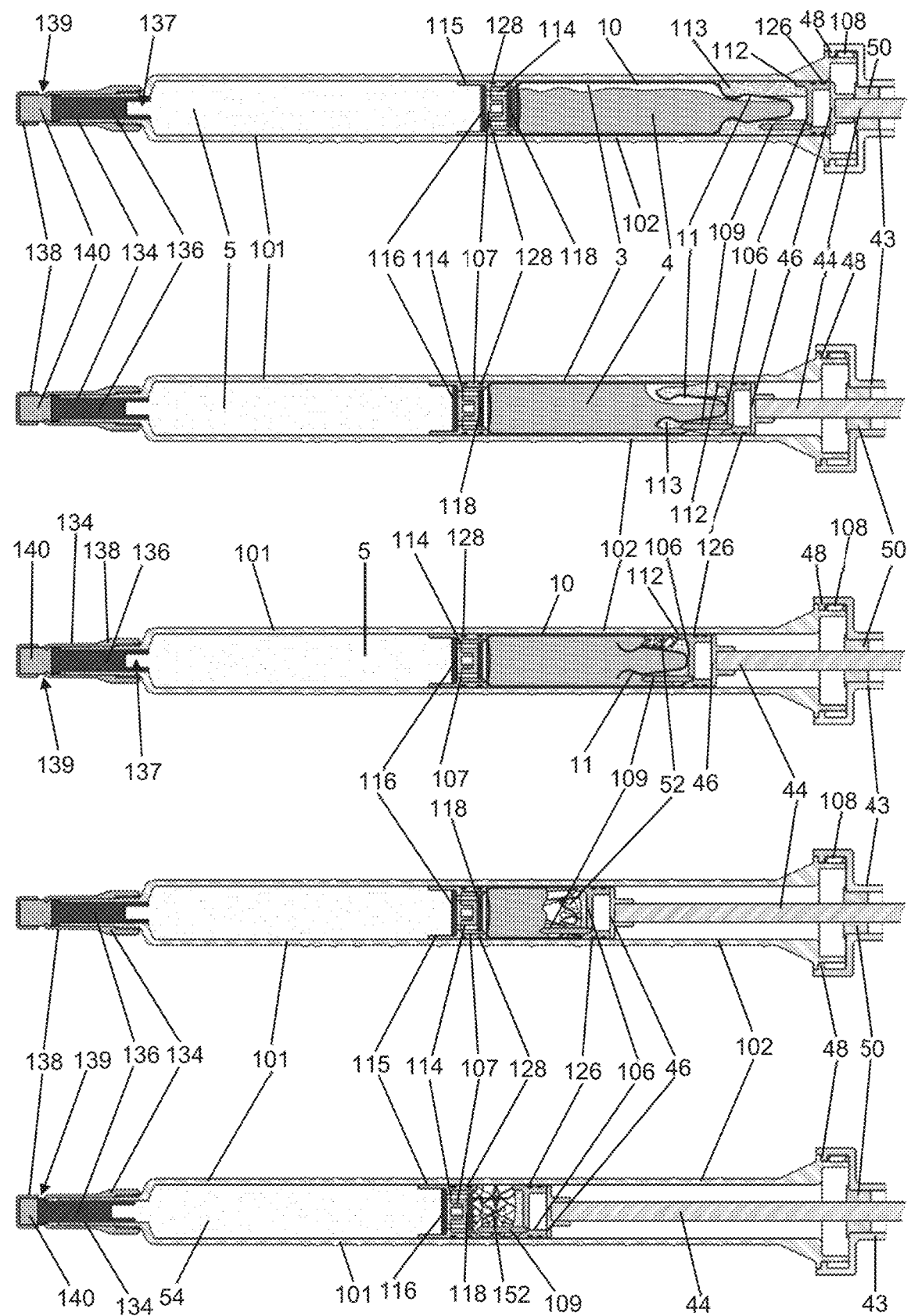
FIG. 12: illustrates five schematic cross-sectional views of the second device according to one embodiment as per FIGS. 10 to 11 with an extrusion device connected, one above the other, to illustrate the sequence of a method according to one embodiment.
Figure 13:
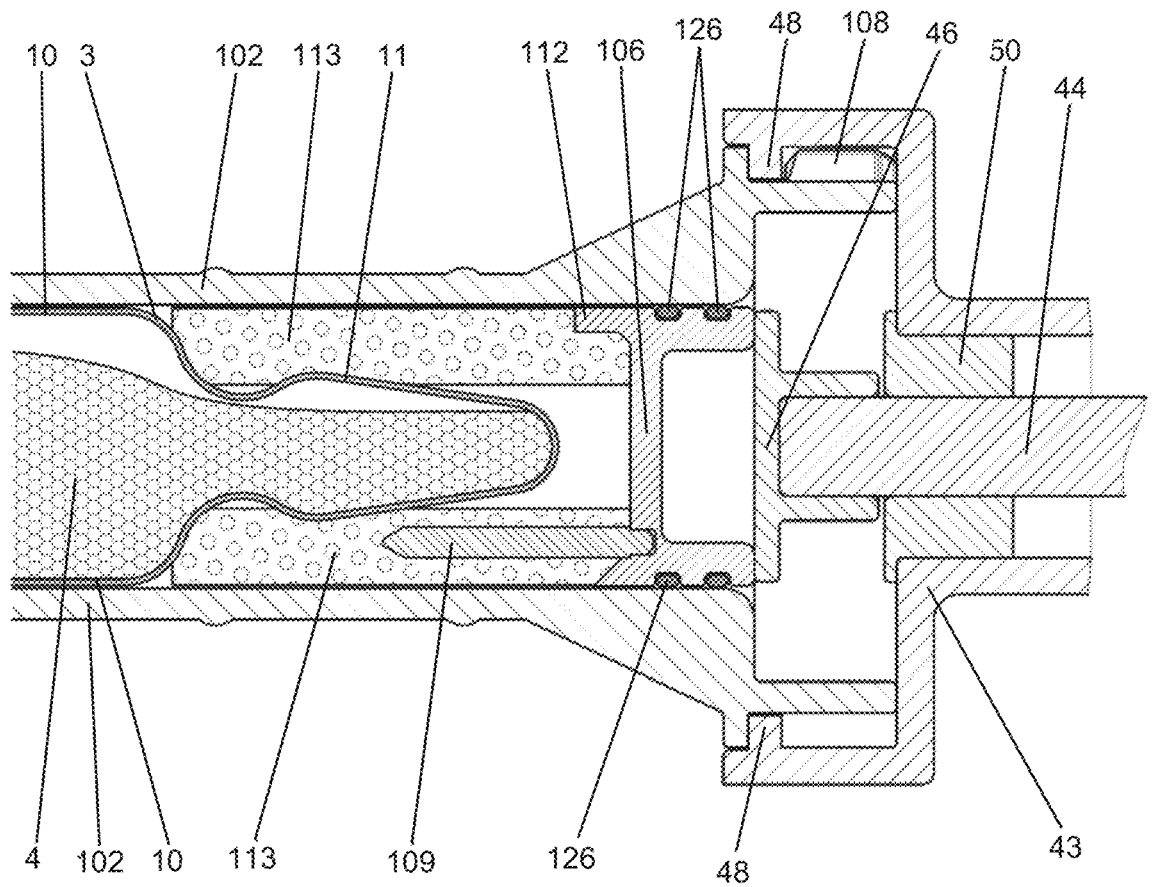
FIG. 13: illustrates a schematic cross-sectional view as a section enlargement of the second device according to one embodiment as per the first illustration from the top in FIG. 12, which is connected to the extrusion device.
Figure 14:
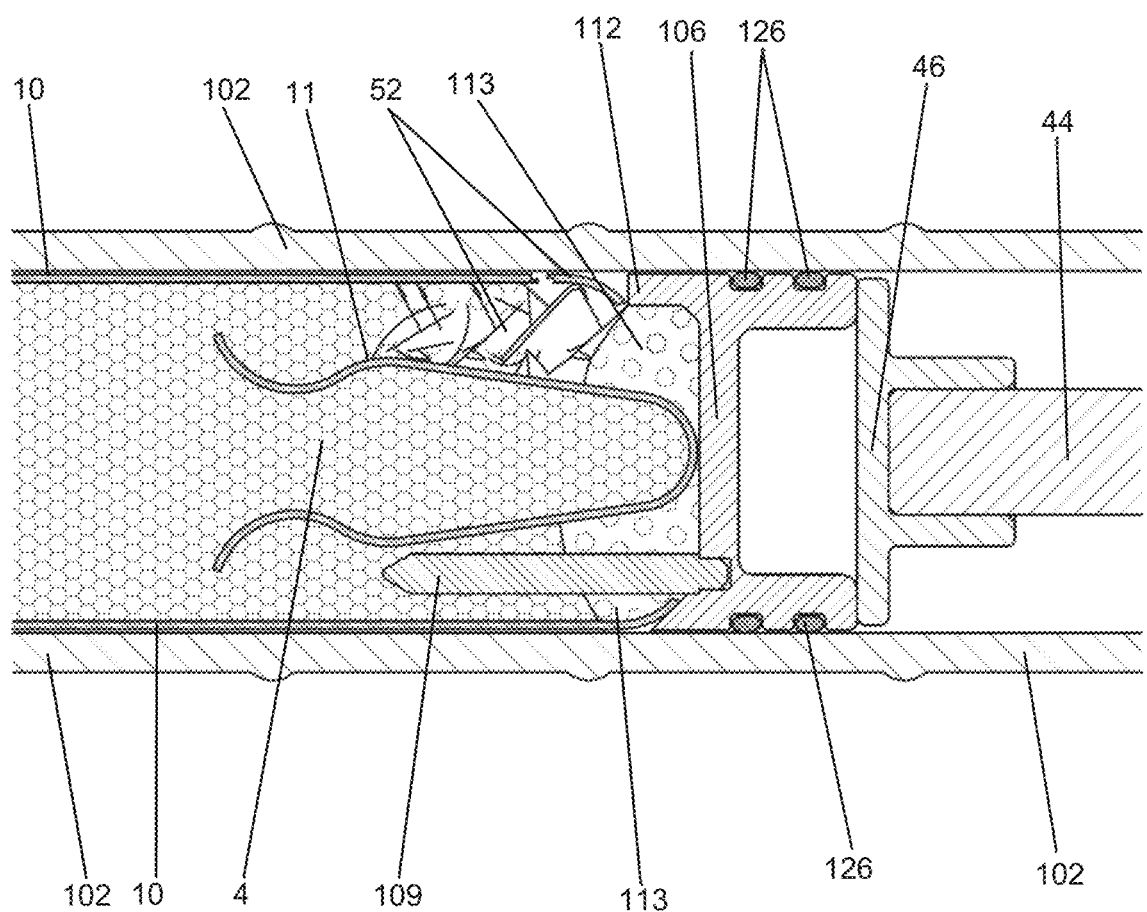
FIG. 14: illustrates a schematic cross-sectional view as a section enlargement of the second device according to one embodiment as per the third illustration from the top in FIG. 12, while the ampoule is being broken open.
Figure 15:
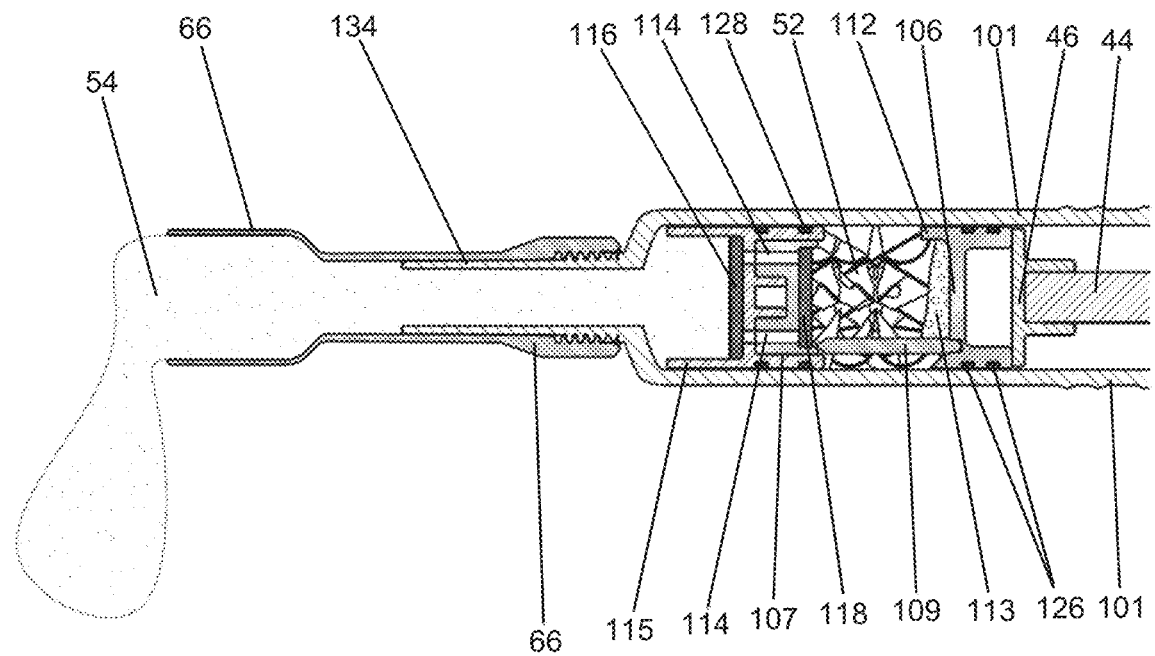
FIG. 15: illustrates a schematic cross-sectional view as a section enlargement of the front part of the second device according to one embodiment as per FIGS. 10 to 14 after the extrusion of the bone cement paste, with dispensing tip attached.
Figure 16:
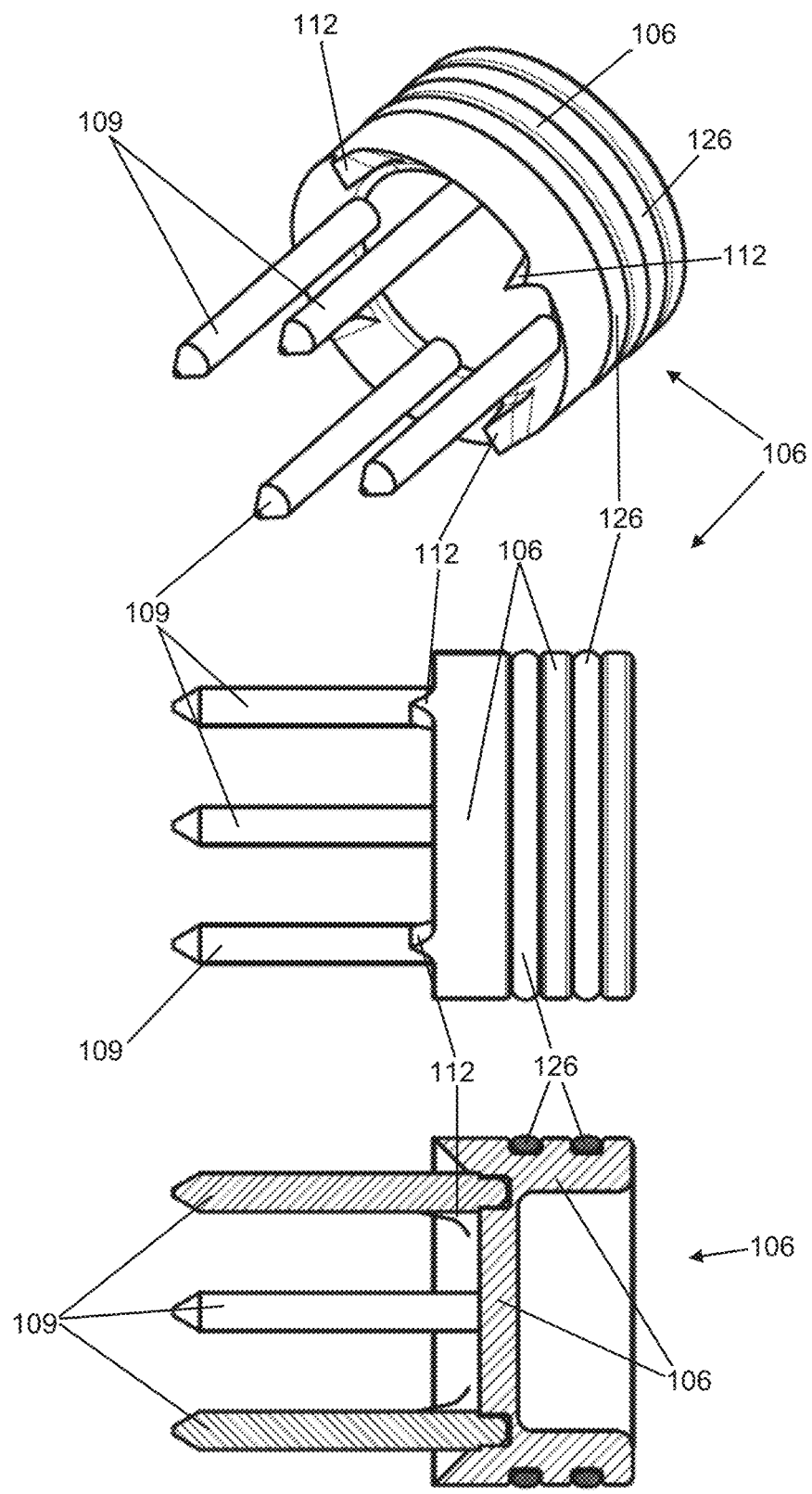
FIG. 16: a perspective view (top), a side view (centre) and a cross-sectional view (bottom) of the pumping plunger of the second device according to one embodiment as per FIGS. 10 to 15.

The FIGS. 10 to 16 depict illustrations of a second device according to one embodiment to store and mix a bone cement paste. The FIGS. 10 to 12 depict different schematic overall views of the second exemplary device according to one embodiment. FIGS. 13 to 15 depict section enlargements of schematic cross-sectional views as detailed views of different regions of the second device according to one embodiment, and FIG. 16 illustrates three schematic detailed views of a pumping plunger of the second device according to one embodiment. The second device according to one embodiment corresponds to a very large extent to the design of the first device according to one embodiment as far as the external design is concerned and completely as far as the starting components are concerned.

The second device according to one embodiment consists mainly of a tubular plastic container which forms a cartridge 101 with a cylindrical interior as its front part (in FIG. 10 at the top, in FIG. 11 at the bottom left, and in FIGS. 12 to 15 on the left), and which forms as its rear part a receptacle 102 with a cylindrical interior for a glass ampoule 3 (or a plastic ampoule 3) as a container for a monomer liquid 4. The rear of the device is illustrated at the bottom in FIG. 10, at the top right in FIG. 11, and on the right in FIG. 12. The tubular shape of the container can be recognised particularly well in the cross-sectional views of FIGS. 10 and 11. The interior of cartridge 101 as well as the interior of the receptacle 102 are cylindrical with a circular base. The diameters of the interior of the cartridge 101 and the diameter of the interior of the receptacle 102 are equal in size and flush with each other. The container with the receptacle 102 and the cartridge 101 is in one embodiment made of plastic by injection moulding. The receptacle 102 thus has a cylindrical interior into which the glass ampoule 3 is inserted. The monomer liquid 4 is contained in the glass ampoule 3. A cement powder 5 is filled or in one embodiment pressed into the interior of the cartridge 101. The monomer liquid 4 and the cement powder 5 form the starting components for a PMMA bone cement which can be produced with the device. The glass ampoule 3 means the monomer liquid 4 can be stored for a very long time in the receptacle 102 and thus in the device. The cement powder 5 can likewise be stored in the device over longer periods of time. The device is therefore suitable for the storage of the monomer liquid 4 and the cement powder 5 as starting components of a bone cement paste of the PMMA bone cement. The device is also suitable for and provides for the mixing of the bone cement paste from the starting components and the dispensing of the mixed bone cement paste as well, however.

A pumping plunger 106 made of synthetic material which can move in the longitudinal direction in the cylindrical interior of the receptacle 102 is arranged in the receptacle 102. The pumping plunger 106 is arranged close to the rear of the receptacle 102. The glass ampoule 3 can be compressed and thereby shattered with the pumping plunger 106 in the receptacle 102 by pressing the pumping plunger 106 towards the front, that is, in the direction of the cartridge 101. The pumping plunger 106 has skimmers at the front with which shards 52 of the glass ampoule 3 are skimmed off the inner wall of the receptacle 102. To this end, the skimmers come into contact with the side of the inner wall of the interior of the receptacle.

A dispensing plunger 107 made of synthetic material is arranged in the interior of the cartridge 1 at its rear (in FIG. 10 downwards, in FIG. 11 towards the top right, in FIGS. 12 to 15 towards the right), the plunger being depicted in detail in the illustrations after FIG. 16. A means of fastening 108 is provided on the rear of the receptacle 102 with which the receptacle 102 can be connected to an extrusion device 43 (not visible in FIGS. 10 and 11, see FIG. 12, however). The means of fastening 108 is in one embodiment suitable for and provided to form a bayonet coupling. This allows the pumping plunger 106, which is freely accessible from the rear of the receptacle 102, to be driven forwards with the extrusion device 43 towards the front of the cartridge 101.

On the front of the pumping plunger 106 are four rods 109 as spacers which determine the separation between the dispensing plunger 107 and the pumping plunger 106 when the pumping plunger 106 is pushed fully towards the dispensing plunger 107 (see FIG. 15). The rods 109 extend at least 10 mm from the front of the pumping plunger 106 into the receptacle 102. The rods 109 are rotationally symmetric (for example cylindrical), but can also have an angular cross-section. The rods 109 taper towards the dispensing plunger 107, the tips having a blunt end (see FIG. 16). The tapered tips of the rods 109 mean it is easier to push the shards 52, which are produced between the tips of the rods 109 and the dispensing plunger 107 when the glass ampoule 3 is crushed by the movement of the pumping plunger 106, past the sides of the rods 109. The blunt end of the rods 109 prevents the rods 109 from being pressed into the dispensing plunger 107 or the rods 109 being deformed at the tip, and thus the length of the rods 109 changing and hence the separation between the dispensing plunger 107 and the pumping plunger 106, and thus the space in between varying and becoming not as predictable. This means that the quantity of monomer liquid 4 which remains after the extrusion (see FIG. 15) in the space between the dispensing plunger 107 and the pumping plunger 106 and thus the quantity of the monomer liquid 4 pressed into the cement powder 5 is known very precisely and thus predictable. The consistency of the bone cement paste 54 produced can be adjusted and reproduced very precisely.

The glass ampoule 3 has an ampoule body 10 and an ampoule head 11 which are connected with each other via a thin neck. The glass ampoule 3 can be opened very simply by breaking the ampoule head 11 off the ampoule body 10. The rods 109 run past the side of the ampoule head 11 and surround it (see FIGS. 10, 11 and 12) so that the rods 109 remain arranged at the side of the ampoule head 11 when the glass ampoule 3 moves as a result of the pumping plunger 106 being driven forwards, and are driven into the shoulders of the glass ampoule 3 into the ampoule body 10 (see FIGS. 12 and 14). For the second exemplary device, the glass ampoule 3 is arranged the other way round in the receptacle 102 when compared to the glass ampoule 3 for the first exemplary device as per FIGS. 1 to 9. The fundamental principle is that the ampoule head 11 is namely always oriented in the direction of the rods 9, 109, regardless of whether these are fastened to the dispensing plunger 7 or the pumping plunger 106.

The rods 109 can be elastically deformed and are manufactured from a synthetic material. The elastic deformability allows fragments of the glass ampoule 3 to be guided more easily past the rods 109. The rods 109 are separated at least so far from the inner wall of the receptacle 102 that the wall of the ampoule body 10 fits between the rods 109 and the inner wall of the receptacle 102. The rods 109 thus run in the interior of the ampoule body 10 when the pumping plunger 106 is driven forwards.

There can be provision for the rods 109 to be connected with each other via at least one shared ring (not illustrated). The at least one ring is arranged so as to be parallel to the front of the pumping plunger 106. Two rings can be provided, for example, a first ring having a separation from the front of the pumping plunger 106 of one third of the length of the rods 109, and a second ring having a separation from the front of the pumping plunger 106 of two thirds of the length of the rods 109. The rods 109 are thus stabilised and do not buckle as easily. The longer the rods 109, the more advantageous is a stabilisation with at least one ring. The inner diameter of the at least one ring must be large enough to be able to accept the ampoule head 11.

Four wedge-shaped cutting elements 112 which are provided to cut or break the ampoule body 10 of the glass ampoule 3 when the pumping plunger 106 is driven forwards, are arranged on the front of the pumping plunger 106. The edges of the cutting elements 112 run radially outwards and are arranged on the outside of the pumping plunger 106 so that the edges of the cutting elements 112 can run through the whole wall of the ampoule body 10 and thus cause it to shatter. The tips of the rods 109 are separated from the cutting elements 112 in the longitudinal direction of the device so that the breaking front on which the ampoule body 10 is crushed is separated from the tips of the rods 109. This prevents large quantities of shards 52 from being produced between the tips of the rods 109 and the dispensing plunger 107, which could be trapped between the tips of the rods 109 and the dispensing plunger 107 and thus have an impact on the minimum volume between the pumping plunger 106 and the dispensing plunger 107 and hence the quantity of monomer liquid 4 pressed into the cement powder 5.

A holder 113 in the form of a sleeve of plastic foam is provided for impact protection so the glass ampoule 3 can be stably stored. The sleeve-shaped holder 113 surrounds the ampoule head 11 and is inserted between the rods 109 and the inner wall of the receptacle 102. The holder 113 is permeable to the monomer liquid 4 and manufactured from a synthetic material.

The cartridge 101 and the receptacle 102 are designed in one piece as a combined part made of synthetic material. For the monomer liquid 4, the receptacle 102 and the cartridge 101 are connected so as to be permeable to liquids via a connection 114 in the dispensing plunger 107. A hollow cylinder 115 is arranged on the front of the dispensing plunger 107. The connection 114 through the dispensing plunger 107 leads through a pore filter 116 which is impermeable to the cement powder 5 but permeable to the monomer liquid 4, into the interior of the cartridge 101.

Where the connection 114 joins, a filter 118 is arranged in the dispensing plunger 107 with which the shards 52 of the glass ampoule 3 can be retained. A sieve can also be provided instead of the filter 118 or in addition to the filter 118.

Several ventilation apertures 120 are provided in the wall of the receptacle 102 through which the interior of the receptacle 102 can be sterilised with the aid of a sterilising gas such as ethylene oxide. The ventilation apertures 120 are arranged in the immediate vicinity of the pumping plunger 106 so that the pumping plunger 106 slides directly in front of the ventilation apertures 120 and thus seals the ventilation apertures 120 directly when the pumping plunger 106 is driven forwards in the direction of the cartridge 101. This prevents monomer liquid 4 being discharged through the ventilation apertures 120 when the glass ampoule 3 in the receptacle 102 is opened.

The cylindrical pumping plunger 106 has an outer circumference matching the cylindrical geometry of the interior of the receptacle 102 and is sealed via two circumferential seals 126 against the inner wall of receptacle 102 so as to be liquid tight. The dispensing plunger 107 is also sealed via two circumferential seals 128 against the inner wall of the cartridge 101 so as to be liquid tight. These seals 126, 128 serve to prevent monomer liquid 4 or bone cement paste 54 from being discharged in order to prevent the environment (the operating theatre and the user) from being contaminated. The seals 126, 128 can consist of rubber for this purpose.

At the front, the interior of the cartridge 101 leads into a dispensing tube 134 which restricts a front dispensing aperture of the cartridge 101. The dispensing tube 134 has an external thread at its base. In the inside of the dispensing tube 134, a pore filter 136 is arranged as the seal for the cartridge 101. The pore filter 136 is impermeable to the cement powder 5 but permeable to gases. A recess 137 is provided in the rear of the pore filter 136. The cement powder 5 is also contained in the recess 137. A cap 138 is fastened on the external thread of the dispensing tube 134, the front part of the cap 138 being filled with polystyrene or plastic foam 140. Two wings 142 are provided on the cap 138 so that the cap 138 can easily be screwed off the dispensing tube 134 like a wing nut. The cap 138 has lateral apertures 139. This design allows the interior of the cartridge 101 and the cement powder 5 to be sterilised with the aid of ethylene oxide since the apertures 139 in the cap 138, the polystyrene or the plastic foam 140, the pore filter 136, and the spaces between the powder particles of the cement powder 5 are permeable to air. At the same time, air can be expelled from the receptacle 102 through the cement powder 5, the pore filter 136, the polystyrene or the plastic foam 140, and the apertures 139 in the cap 138, when the pumping plunger 106 is pressed in the direction of the receptacle 101. The cap 138 together with the polystyrene or plastic foam 140 and with the pore filter 136 forms a seal for the dispensing aperture of the cartridge 101 or for the dispensing tube 134.

The cement powder 5 is enclosed in the cartridge 101, since all apertures 139 and connections 114 are sealed with the aid of the pore filters 116, 136 so as to be impermeable to the cement powder 5. The contents of the cartridge 101 can be sterilised by evacuation and rinsing with ethylene oxide. This means the device is also suitable for the long-term storage of the cement powder 5.

FIG. 12 illustrates five schematic cross-sectional views of the second device according to one embodiment as per FIGS. 10 to 16, one above the other, to illustrate the sequence of a method according to one embodiment. As the last step of the method, a state is ultimately reached which is depicted in FIG. 15 as a section enlargement. In this context, FIG. 13 illustrates a section enlargement of the top illustration of FIG. 12, and FIG. 14 a section enlargement of the third illustration from the top in FIG. 12.

At the start of the method, the device is in the starting state, as is illustrates in FIGS. 10 and 11 as well. In this state, the device is inserted into an extrusion device 43 according to one embodiment which essentially corresponds to a conventional cartridge gun. This situation is depicted in the top illustration of FIG. 12. The extrusion device 43 has a rod 44 which can be driven forwards linearly. Only the front part of the extrusion device 43 is illustrated. The extrusion device 43 is the same as the extrusion device 43 which was described in the description of the first example embodiment as per FIGS. 1 to 9, and also includes a handle and a toggle lever (not illustrated in the illustrations) to drive the rod 44 of the extrusion device 43 manually, as happens with conventional manually driven extrusion devices 43 as well. The device is fastened with the means of fastening 108 on the extrusion device 43 (see top illustration in FIG. 12 and FIG. 13). A flat plate 46 is provided on the tip of the rod 44 to drive the pumping plunger 106. With the plate 46, the rod 44 presses against the pumping plunger 106 when the rod 44 is pressed into the receptacle 102 by the extrusion device 43. For this purpose, the extrusion device 43 is connected to the rear of the receptacle 102 via a counter-fastening means 48 so that the plate 46 presses onto the pumping plunger 106 when the rod 44 is driven forwards and propels it in the direction of the cartridge 101. The rod 44 is mounted against a bearing 50 and above it against the counter-fastening means 48 and thus against the receptacle 102 so as to be linearly moveable.

The extrusion device 43 is operated and thus the rod 44, and with the rod 44 the pumping plunger 106 is driven forwards towards the cartridge 101. Since the glass ampoule 3 at its rear is in contact with the pumping plunger 106, the glass ampoule 3 is driven towards the dispensing plunger 107 by the pumping plunger 106. The rods 109 remain arranged on the side of the ampoule head 11 here. At the same time, the interior of the receptacle 102 is reduced in size and the glass ampoule 3 breaks after the base of the glass ampoule 3 is pressed against the dispensing plunger 107. In this process, the ampoule head 11 of the ampoule body 10 first breaks off and is pressed into the ampoule body 10 guided by the rods 109. The monomer liquid 4 discharges from the glass ampoule 3 into the interior of the receptacle 102. The dispensing plunger 107 cannot be pushed or cannot be pushed far in the direction of the pore filter 136 by the glass ampoule 3 when the cement powder 5 is dry, that is, is not wetted by the monomer liquid 4, since the dry cement powder 5 is not free-flowing and blocks any movement of the dispensing plunger 107. This situation is illustrated in the second illustration from the top in FIG. 12.

Residual air from the receptacle 102 is expelled from the device through the filter 118, the connection 114, the pore filter 116, through the spaces between the particles of the cement powder 5, through the pore filter 136, through the plastic foam 140 and out of the apertures 139 in the cap 138.

As the pumping plunger 106 is driven further forwards, the rods 109 glide into the ampoule body 10. Simultaneously, the space between the pumping plunger 106 and the dispensing plunger 107 is reduced further, pressing air out of the space in the process. When the air has escaped completely, the monomer liquid 4 released is pressed out of the receptacle 102 into the interior of the cartridge 101 and thus into the cement powder 5. Here the monomer liquid 104 can flow along the hollow cylinder 115 deep into the cement powder 5. The wall of the ampoule body 10 now meets the cutting elements 112 (see FIG. 12 third illustration from the top and FIG. 14) and is thus shattered at the cutting elements 112 as the pumping plunger 106 and the ampoule body 10 are driven further forwards. The shards 52 are thus produced at a distance from the tips of the rods 109. The shards 52 collect between the tips of the rods 109 and the front of the pumping plunger 106. This situation is depicted in FIG. 12, fourth illustration from the top.

Only small shards 52 of the glass ampoule 3 ultimately remain, which are kept back by the filter 118 and remain in the tubular container which forms the cartridge 101 and the receptacle 102. The monomer liquid 4 is pressed into the cement powder 5 through the filter 118, the connection 114 and the pore filter 116, where it starts to react with the cement powder 5 so that the bone cement paste 54 forms from the mixture (see FIG. 12 bottom illustration). The quantity of monomer liquid 4 is chosen such that the cement powder 5 is wetted with the monomer liquid 4 right into the furthermost tip of the cartridge 101, that is, right into the recess 137 in the pore filter 136. This situation is illustrated in FIG. 12, bottom drawing. As soon as the mixture is produced, the pore filter 136 is driven forwards by the pressure acting on the bone cement paste 54 caused by the pressure on the dispensing plunger 107, and compresses the plastic foam 140. When the pore filter 136 now slides forwards, it becomes visible to the user from the outside through the aperture 139 in the cap 138. This situation can be seen in FIG. 12, bottom drawing. To this end, the pore filter 136 in one embodiment has a different colour and/or brightness to the plastic foam 140. The plastic foam 140 can be blue, for example, and the pore filter 136 yellow.

In this state, the cap 138 with the pore filter 136 and the plastic foam 140 is unscrewed and a dispensing aperture extension in the form of an applicator tube 66 is screwed onto the dispensing tube 134 instead (see FIG. 14). When the cap 138 is unscrewed, the part of the bone cement paste 54 at the very front, which is located in the recess 137 of the pore filter 138, is removed with the cap 138 and the pore filter 136. A part of the bone cement paste 54 which is potentially not mixed as well as the rest is thus removed, thus making the available bone cement paste 54 more homogeneous.

Driving the rod 44 further forwards presses the pumping plunger 106 with the rods 109 against the dispensing plunger 107, which sets the minimum distance between the pumping plunger 106 and the dispensing plunger 107, or their length in the longitudinal direction of the device determines the separation between the pumping plunger 106 and the dispensing plunger 107 and thus the volume enclosed in between. Driving the rods 44 forward even more also drives forward the pumping plunger 106, the shards 52 and the dispensing plunger 107 arranged in front of the pumping plunger 106 and separated by the rods 109. The bone cement paste 54 is then dispensed from the cartridge 101 via the applicator tube 66. To this end, the dispensing plunger 107 is driven forwards with the rod 44 towards the dispensing tube 134 (see FIG. 15). The bone cement paste 54 from the inside of the cartridge 101 is expelled through the dispensing tube 134 and applicator tube 66 and can be applied there or used for further processing.

Finally, the hollow cylinder 115 meets the front inside of the interior of the cartridge 101. The hollow cylinder 115 here encloses a volume of bone cement paste 54 which is closest to the dispensing plunger 107. This bone cement paste 54 is retained in the device. Owing to the forces arising at the end of the extrusion process in the interior of the device, a post-densification can take place and thus a slight change in the consistency of the bone cement paste 54, which causes it to be retained in the cartridge 101. The hollow cylinder 115 produces a dead volume in the interior of cartridge 101 which cannot be expelled from the cartridge 101 through the dispensing aperture and the dispensing tube 134. This dead volume now contains the portion of the bone cement paste 54 which possibly contains too large a proportion of monomer liquid 4. This design ensures that it is not possible to apply bone cement paste 54 with a changing consistency due to a changing composition with the device.

The apertures 139 also act as visual markers which can be used to ascertain when the device is ready for use. When the pore filter 136 is pushed forwards because of the pressure of the bone cement paste 54 and thereby compresses the polystyrene 140 in the cap 138, the pore filter becomes visible through the apertures 139. The user can thus see that the bone cement paste 54 is now fully mixed in the cartridge 101 and is thus ready for use. At that time, the user can unscrew the cap 138 with the pore filter 136 and screw the applicator tube 66 onto the dispensing tube 134. The dispensing plunger 107 can then be driven via the pumping plunger 106 with the rod 44 and hence the bone cement paste 54 can be extruded out of the cartridge 101 through the applicator tube 66.

In accordance with a further alternative according to one embodiment, which to a large extent corresponds to the preceding embodiments, there can be provision for rods as spacers to be connected to each other via a ring which is separate from the dispensing plunger and the pumping plunger. The rods do then not have to be connected with the pumping plunger or the dispensing plunger, but can be arranged as loose and separate spacers between the pumping plunger and the glass ampoule 3 and/or between the dispensing plunger and the glass ampoule 3 in the receptacle. The ring shape and the fact that the loose spacer is attached to the ampoule head 11 and/or the fact that the loose spacer is inserted into a sleeve-shaped holder, such as the sleeve-shaped holders 13, 113 according to the first and the second embodiment, mean that these spacers are also automatically separated from the inner wall of the receptacle by at least as much as the thickness of the wall of the ampoule body 10.

The features of the embodiments disclosed in the above description, and also in the claims, figures and example embodiments, can individually, but also in any arbitrary combination, be important for the realization of its different embodiments.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof

What is claimed is:

1. A device to produce a bone cement paste from a monomer liquid and a cement powder as starting components of the bone cement paste and to dispense the mixed bone cement paste, the device comprising:
 a cartridge with a cylindrical interior, a dispensing plunger which can move towards a front of the cartridge being arranged in the interior of the cartridge in a rear of the cartridge;

a receptacle that extends along a longitudinal direction, a front of the receptacle being connected to the rear of the cartridge;

a pumping plunger arranged in the receptacle, the pumping plunger being held in the receptacle so as to be movable in the longitudinal direction of the receptacle towards the front of the receptacle;

a crushable ampoule containing the monomer liquid, the ampoule being arranged in the receptacle between the pumping plunger and the dispensing plunger and the ampoule having an ampoule body, the ampoule body being in contact with an inner wall of the receptacle at least in parts; and a spacer arranged in the receptacle between the dispensing plunger and the ampoule body or between the pumping plunger and the ampoule body, the spacer extending in the longitudinal direction and the spacer having a separation from the inner wall of the receptacle that is at least as large as a wall thickness of the ampoule body.

2. The device of claim 1, wherein the spacer is fastened on a rear of the dispensing plunger or on a front of the pumping plunger, or wherein the spacer is arranged around an ampoule head of the ampoule, the ampoule head having a smaller outer diameter than the ampoule body.

3. The device of claim 1, wherein at least one cutting element with a cutting edge is arranged on a front of the pumping plunger facing the ampoule and/or on a rear of the dispensing plunger facing the ampoule, wherein the at least one cutting element is arranged on a part of the front of the pumping plunger and/or the rear of the dispensing plunger that is located towards the inner wall of the receptacle so that the at least one cutting element cuts through the wall of the ampoule body when the pumping plunger is driven forward, the cutting edge extending radially away from a central longitudinal axis of the pumping plunger and/or the dispensing plunger.

4. The device of claim 3, wherein the ampoule has an ampoule head with a smaller diameter than the ampoule body, and the at least one cutting element and the spacer are arranged on the rear of the dispensing plunger, the ampoule head pointing in a direction of the dispensing plunger, or the at least one cutting element and the spacer are arranged on the front of the pumping plunger, the ampoule head pointing in a direction of the pumping plunger.

5. The device of claim 3, wherein the spacer in the longitudinal direction is at least three times as long as the at least one cutting element is separated in the longitudinal direction from the front of the pumping plunger or the rear of the dispensing plunger.

6. The device of claim 1, wherein the spacer blocks a further reduction of a separation between the pumping plunger and the dispensing plunger after the ampoule has been broken open and after the ampoule has been compressed as the pumping plunger is driven forwards so that shards of the ampoule can be accommodated between the dispensing plunger and the pumping plunger without being broken into smaller shards when the pumping plunger and the dispensing plunger with the spacer in between are moved towards the front of the cartridge.

7. The device of claim 1, wherein the spacer has a length in the longitudinal direction such that a volume between the pumping plunger and the dispensing plunger at a distance which corresponds to the length of the spacer, is larger than a volume of the ampoule material, or at least as large as a volume of the shards of the broken ampoule including all spaces.

8. The device of claim 1, wherein the spacer comprises a plurality of rods that extend in the longitudinal direction, wherein the rods are connected with each other or are fastened on a front of the pumping plunger or are fastened on a rear of the dispensing plunger, the rods comprising at least one of a round, triangular, angular, and rectangular cross-section.

9. The device of claim 1, wherein the ampoule has an ampoule head that is connected to the ampoule body, where the ampoule head has a smaller outer diameter than the ampoule body and wherein the spacer is arranged next to the ampoule head or the spacer surrounds the ampoule head.

10. The device of claim 1, wherein the ampoule consists of glass or a synthetic material that is chemically stable against the monomer liquid.

11. The device of claim 1, wherein the ampoule body is cylindrical and the receptacle has a cylindrical interior, an outer diameter of the ampoule body being matched to an inner diameter of the cylindrical receptacle in the interior so that the ampoule body is held in the receptacle.

12. The device of claim 1, wherein the pumping plunger is supported so that it can be driven from the rear of the receptacle to the front of the receptacle in the longitudinal direction.

13. The device of claim 1, wherein the rear of the cartridge is connected to the front of the receptacle such that the interior of the cartridge is flush with an interior of the receptacle.

14. The device of claim 1, wherein cement powder in the interior of the cartridge is arranged between the front of the cartridge and the dispensing plunger, and wherein an additive which conducts the monomer liquid being distributed in the cement powder.

15. The device of claim 1, wherein a hollow cylinder is arranged on a front of the dispensing plunger and blocks further movement of the dispensing plunger towards the front of the cartridge so that sections of the dispensing plunger are at a distance from a front of the interior of the cartridge and a dead volume remains in the interior of the cartridge when the dispensing plunger is pushed against the front of the interior of the cartridge.

16. A method of producing a bone cement paste, whereby the bone cement paste is produced from a cement powder and a monomer liquid, the method comprising:

A) pressing a pumping plunger in a longitudinal direction towards a dispensing plunger, wherein an ampoule containing the monomer liquid and a spacer that extends in the longitudinal direction in a receptacle are arranged between the pumping plunger, which can move in the longitudinal direction, and the dispensing plunger;

B) wherein movement of the pumping plunger towards the dispensing plunger causes an ampoule head of the ampoule to be broken open or broken off, a free end of the spacer being moved inside the opened ampoule against an ampoule body of the opened ampoule so that at least a part of a wall of the ampoule body is arranged between the spacer and an inner wall of the receptacle during the movement;

C) wherein the opened ampoule is compressed and further broken by the movement of the pumping plunger towards the dispensing plunger, and the monomer liquid is thus squeezed out of the receptacle and into the cement powder, where it mixes with the cement powder to form the bone cement paste; and D) wherein the spacer is clamped between the pumping plunger and the dispensing plunger and thus prevents a further reduction of a separation of the dispensing plunger to the pumping plunger and thus a further discharge of monomer liquid from the receptacle into the bone cement paste.

17. The method of claim 16, wherein the method produces a pasty polymethyl methacrylate bone cement paste.

18. The method of claim 16, wherein in C) the monomer liquid is pressed through a connection in the dispensing plunger which is impermeable to the cement powder but permeable to gases and the monomer liquid, into a cartridge which contains the cement powder.

19. The method of claim 16, wherein the movement of the pumping plunger in B) and C) is driven by an axial movement of a rod of an extrusion device which is fastened on the receptacle before A).

20. The method of claim 16, wherein at least one cutting element with a cutting edge is arranged on a rear of the dispensing plunger or on a front of the pumping plunger, whereby in C) the wall of the ampoule body is cut or broken with the cutting edge, the free end of the spacer having a separation in the longitudinal direction of at least 10 mm to the at least one cutting element.

21. The method of claim 16, wherein the cement powder is arranged in an inner chamber of a cartridge, the dispensing plunger is arranged in an interior of the cartridge so it can be moved, where in C) the monomer liquid is pressed into the interior of the cartridge and where after D) the dispensing plunger is pressed in the longitudinal direction into the interior of the cartridge by the pumping plunger, and thus the bone cement paste is extruded from the interior of the cartridge.

* * * * *